(12) United States Patent
Cunningham et al.

(10) Patent No.: US 9,796,740 B2
(45) Date of Patent: Oct. 24, 2017

(54) LIQUID BISACYLPHOSPHINE OXIDE PHOTOINITIATOR

(71) Applicant: BASF SE, Ludwigshafen (DE)

(72) Inventors: Allan F. Cunningham, Magden (CH); Katharina Misteli, Schopfheim (DE); Kurt Dietliker, Allschwil (CH); Beat Grimm, Muttenz (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/903,637

(22) PCT Filed: Jun. 30, 2014

(86) PCT No.: PCT/IB2014/062730
§ 371 (c)(1),
(2) Date: Jan. 8, 2016

(87) PCT Pub. No.: WO2015/004566
PCT Pub. Date: Jan. 15, 2015

(65) Prior Publication Data
US 2016/0168177 A1    Jun. 16, 2016

(30) Foreign Application Priority Data

Jul. 8, 2013   (EP) .................................. 13175468

(51) Int. Cl.
*C08F 2/46*    (2006.01)
*C08F 2/50*    (2006.01)
(Continued)

(52) U.S. Cl.
CPC .............. *C07F 9/5337* (2013.01); *C08F 2/50* (2013.01); *C09D 4/00* (2013.01); *G03F 7/027* (2013.01); *G03F 7/029* (2013.01)

(58) Field of Classification Search
CPC . C07F 9/5337; C08F 2/50; C09D 4/00; G03F 7/027
(Continued)

(56) References Cited

U.S. PATENT DOCUMENTS 3,844,916 A    10/1974  Gaske
4,218,218 A    8/1980   Daubach et al.
(Continued)

FOREIGN PATENT DOCUMENTS

CA    2159265 A1    3/1996
CN    103073658 A   5/2013
(Continued)

OTHER PUBLICATIONS

International Search Report for PCT/IB2014/062730 mailed Dec. 1, 2014.
(Continued)

*Primary Examiner* — Jessica E Whiteley
(74) *Attorney, Agent, or Firm* — Drinker Biddle & Reath LLP

(57) ABSTRACT

A photoinitiator mixture comprising the components
(a) a compound of the formula (I)

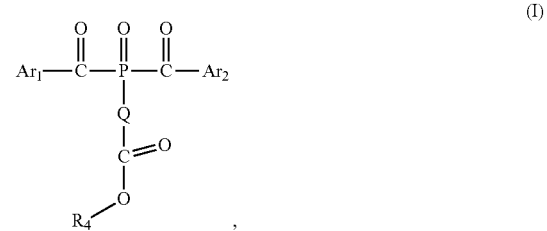

wherein
$Ar_1$ and $Ar_2$ independently of each other are

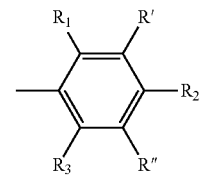

or naphthyl which is unsubstituted or substituted one or more times by $R_1$, $R_2$, $R_3$ or R'; $R_1$ and $R_3$ independently of each other are $C_1$-$C_4$alkyl, $C_1$-$C_4$alkoxy or halogen; $R_2$ is hydrogen, $C_1$-$C_4$alkyl, halogen, $C_1$-$C_4$alkoxy or $C_2$-$C_{20}$alkoxy which is interrupted by one or more O; Q is $C_1$-$C_4$alkylene; $R_4$ is methyl or ethyl; R' and R" independently of each other are hydrogen or PG-Y—R'"—X—; PG is a polymerizable group or methyl or ethyl; Y is a direct bond, O or S; X is a direct bond, O or S; R'" is a direct bond, $C_1$-$C_{20}$alkylene or $C_2$-$C_{20}$alkylene which is interrupted by one or more O;
(b) one or more compounds of the formula (II)

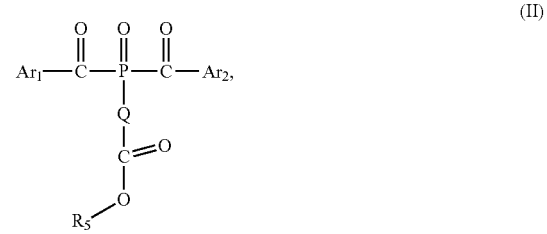

wherein
$Ar_1$, $Ar_2$ and Q are as defined above, and $R_5$ is for example $C_3$-$C_{30}$alkyl which is unsubstituted or substituted and (Continued)

(c) optionally a compound of the formula (III)

$$R_5\text{—OH} \quad (III),$$

wherein $R_5$ is as defined above; provides a liquid photointiator.

14 Claims, No Drawings

(51) Int. Cl.
*C08G 61/04* (2006.01)
*C07F 9/53* (2006.01)
*G03F 7/029* (2006.01)
*G03F 7/027* (2006.01)
*C09D 4/00* (2006.01)

(58) Field of Classification Search
USPC ...... 522/11, 28, 7, 6, 71, 189, 184, 1; 520/1
See application file for complete search history.

(56) References Cited

U.S. PATENT DOCUMENTS

| | | | |
|---|---|---|---|
| 4,287,039 | A | 9/1981 | Buethe et al. |
| 4,339,566 | A | 7/1982 | Rosenkranz et al. |
| 4,384,056 | A | 5/1983 | Schmidt et al. |
| 4,575,330 | A | 3/1986 | Hull |
| 4,737,593 | A | 4/1988 | Ellrich et al. |
| 4,753,817 | A | 6/1988 | Meixner et al. |
| 5,013,768 | A | 5/1991 | Kiriyama et al. |
| 5,186,846 | A | 2/1993 | Brueckmann et al. |
| 5,482,649 | A | 1/1996 | Meixner et al. |
| 5,538,548 | A | 7/1996 | Yamazaki |
| 5,587,404 | A | 12/1996 | Kröner et al. |
| 5,620,751 | A | 4/1997 | Brindoepke et al. |
| 5,734,002 | A | 3/1998 | Reich et al. |
| 5,922,473 | A | 7/1999 | Muthiah et al. |
| 6,294,592 | B1 | 9/2001 | Herrmann et al. |
| 6,306,555 | B1 | 10/2001 | Schulz et al. |
| 2005/0256218 | A1* | 11/2005 | Lachowicz ............... C08F 2/50 522/6 |
| 2007/0027229 | A1 | 2/2007 | Moszner et al. |
| 2008/0004464 | A1* | 1/2008 | Murer ................... C07F 9/5036 560/51 |

FOREIGN PATENT DOCUMENTS

| | | |
|---|---|---|
| DE | 2936039 A1 | 4/1981 |
| DE | 4228514 A1 | 3/1994 |
| DE | 19700064 A1 | 7/1997 |
| DE | 19727767 A1 | 1/1999 |
| EP | 012339 A1 | 6/1980 |
| EP | 033896 A1 | 8/1981 |
| EP | 041125 A1 | 12/1981 |
| EP | 126541 A1 | 11/1984 |
| EP | 245639 A2 | 11/1987 |
| EP | 280222 A2 | 8/1988 |
| EP | 339841 A2 | 11/1989 |
| EP | 438123 A2 | 7/1991 |
| EP | 636669 A2 | 2/1995 |
| EP | 678534 A1 | 10/1995 |
| EP | 704469 A2 | 4/1996 |
| EP | 12197968.6 | 12/2012 |
| EP | 2935289 A1 | 10/2015 |
| GB | 2180358 A | 3/1987 |
| GB | 2310855 A | 9/1997 |
| WO | WO-99/03930 A1 | 1/1999 |
| WO | WO-00/10974 A2 | 3/2000 |
| WO | WO-00/20517 A2 | 4/2000 |
| WO | WO-01/42313 A1 | 6/2001 |
| WO | WO-2004/074328 A1 | 9/2004 |
| WO | WO-2006/008251 A2 | 1/2006 |
| WO | WO-2006056541 A1 | 6/2006 |
| WO | WO-2012012067 A1 | 1/2012 |
| WO | WO-2012052147 A1 | 4/2012 |
| WO | WO-2013/020469 A1 | 2/2013 |
| WO | WO-2014095724 A1 | 6/2014 |

OTHER PUBLICATIONS

"Paints and Coatings", Ullmann's Encyclopedia of Industrial Chemistry, '1991, 5th ed., vol. A18, pp. 368-426.
"Paints and Coatings", Ullmann's Encyclopedia of Industrial Chemistry, '1991, 5th ed., vol. A18, pp. 491-500.
"Paints and Coatings", Ullmann's Encylopedia of Industrial Chemistry, 1991, 5th ed., vol. A18, pp. 469.
Bielmann"Katalytisch wirksame Verbindungen", Lackadditive, Wiley-VCH Verlag, Weinheim, 1998, pp. 244-247.
Moszner, N., et al., "Synthesis of bis(34[2-(allyloxy)ethoxy]methyl}-2,4,6-trimethylbenzoyl)(phenyl)phospine oxide-a tailor-made photoinitiator for dental adhesives", Belistein Journal of Organic Chemistry, 2010, vol. 6, No. 26, pp. 1-9.
Otera, J., "Transesterification", Chem. Rev., 1993, vol. 93, pp. 1449-1470.
Schuchardt, U., et al., "Transesterification of Vegetable. Oils: a Review", J. Braz. Chem. Soc., 1998, vol. 9, No. 1, pp. 199-210.
M. Wittig, Th. Gohmann, Radiation Curing of Powder Coating, Conference Proceedings, Radtech Europe 1993.

* cited by examiner

LIQUID BISACYLPHOSPHINE OXIDE PHOTOINITIATOR

CROSS-REFERENCE TO RELATED APPLICATIONS

This application is a national stage application (under 35 U.S.C. §371) of PCT/IB2014/062730, filed Jun. 30, 2014, which claims benefit of European Application No. 13175468.1, filed Jul. 8, 2013, both of which are incorporated herein by reference in their entirety.

The present invention relates to new, liquid bisacylphosphine oxide photoinitiators, the preparation and use of such compounds.

As the technology of the mono- and bisacylphosphine oxide compounds is becoming increasingly important owing to the excellent photoinitiator properties of these compounds there is also a need for a liquid, easy to use form of such photoinitiators with an improved performance in the application and curing process.

Bisacylphosphine oxide photoinitiator compounds are for example described in U.S. Pat. No. 4,737,593.

Most bisacylaphosphine oxide (BAPO) photoinitiators known so far are solid compounds. As an example, phenyl-bis(2,4,6-trimethylbenzoyl)-phosphine oxide (Irgacure® 819) is a yellowish solid with a melting point of 127-132° C. While these compounds are highly appreciated for their curing performance, it is well known to the person skilled in the art that many of these compounds are difficult to dissolve and to incorporate into a radiation curable formulation. Thus the preparation of radiation curable formulations containing these photoinitiators is often a tedious process, requiring a long time and/or higher temperatures in order to homogeneously incorporate the photoinitiator. In addition, handling of powdery solid compounds in an application process is complex since appropriate measures to avoid dust formation have to be taken. A liquid form of a bisacylphosphine oxide photoinitiator with the same or better performance as the known solid derivates that can be used in a simple stir-in process thus is highly appreciated.

Moreover it is often advantageous to use bisacylphosphine oxide photoinitiators in combination with other types of photoinitiators in order to achieve an optimum curing performance. Widely used combinations are for example blends of α-hydroxy ketone compounds with bisacylphosphine oxide compounds as they are for example described in GB2310855. In order to provide an optimum performance a blend must be applied in a homogenous form, which is difficult to obtain by the simple mixing of two or more photoinitiator components. Highest homogeneity is obtained if the blend is a liquid, and thus most photoinitiator combinations containing a bisacylphosphine oxide photoinitiator are liquids. Liquid blends can be obtained by either dissolving the solid bisacylphosphine oxide photoinitiator in another liquid photoinitiator or a photoinitiator blend which is of liquid form. Alternatively it is well known that mixtures of two or more solid components may form a liquid if they are blended in the ratio of a eutectic mixture with a melting point sufficiently below the handling temperature. A drawback of such liquid blends containing a component of relatively poor solubility is the fact that they are usually only stable within a limited range of the mixing ratio. Pronounced changes in the environmental conditions during storage such as temperature may result in the crystallisation of low soluble components, rendering the mixture inhomogeneous and thus unusable. Moreover, the limited range of mixing ratios prevents the optimization of the product ratio as required for an optimum curing performance. Thus there is a need for a liquid bisacylphosphine oxide photoinitiator that allows to considerably expand the mixing ratio for producing liquid blends with other photoinitiators, with unlimited possibilities in particular if the other photoinitiator components are also liquid.

Therefore many efforts to produce liquid bisacylphosphine oxide photoinitiators have been reported. In fact the introduction of suitable substituents on the bisacylphosphine oxide structure results in compounds which are not crystalline. However, while these compounds are not solid, due to the size of the molecule they usually are highly viscous resins or lacquers which cannot easily be handled e.g. by pouring. These compounds in fact have to be solubilised by adding suitable diluents such as a solvent, or by heating to a temperature where the viscosity is sufficiently low. Such conditions are not acceptable for a technical application.

Liquid bisacylphosphinne oxide photoinitiators for use in dental applications have recently been reported in US2007/0027229 and in Beilstein J. Org. Chem 2010, 6, 26 by N. Moszner et al. The structures carry selected substituents on the benzoyl and/or P-aryl moieties, for example flexible alkyl substituents interrupted by heteroatoms such as oxygen. The substituted benzoyl and/or P-aryl compounds used for the synthesis of the bisacylphosphine oxide structures have to be prepared in multistep synthetic sequences.

A paper entitled "Liquid Bis-Acylphosphine Oxide (BAPO) Photoinitiators" has been presented by C. C. Chiu at RadTech USA 2010. However the liquid photoinitiator reported is in fact a mixture of a bisacylphosphine and the corresponding bisacylphosphine oxide (Irgacure® 819). While such a mixture is liquid, it is well known that bisacylphosphines are easily oxidized upon standing in an oxygen containing atmosphere to give the corresponding bisacylphosphine oxide. Thus such a blend of a bisacylphosphine and a bisacylphosphine oxide is not stable upon storage but will be converted into the solid bisacylphosphine oxide. This poor chemical stability limits its industrial applications such as coatings.

Recently bisacyl phosphinic esters carrying a P-OR substituent have been claimed as liquid BAPO photoinitiators. While the preparation of liquid bisacylphosphinic acid ester photoinitiators as claimed in the WO2012/012067 is desirable in view of the aforementioned limitations of solid bisacylphosphine oxides, WO 2012/012067 discloses only bis(2,4,6-trimethylbenzoyl)-n-butoxy phosphine oxide. However compounds of this class carrying short or medium alkyl chains, such as for example an ethyl or a hexyl group, are solid and not liquid compounds (see for example the compounds disclosed in European Patent Application No. 12197968.6. Moreover, the synthetic access reported is rather cumbersome and expensive and does not provide a flexible approach allowing the easy fine tuning of application properties.

Similar bisacylphosphinic acid ester derivatives have also been claimed in WO 2013/020469 (T. Chen, Y. Wang). However, the liquid bisacylphosphine oxide structures claimed in WO 2012/012067 and the BAPO claimed in WO 2013/020469 are limited to bisacylphosphinic acid ester derivatives and do not encompass P-R substituted derivatives with R being a substituent bound via a carbon atom to the phosphors atom of the bisacylphosphine oxide structure. It is well known that the substituent on the phosphorous atom in acylphosphine oxide photoinitiators has a decisive influence on the application properties of the compound as photoinitiator. This becomes obvious for example in the different efficiencies of the monoacylphosphine oxide (2,4, 6-trimethylbenzoyl)-diphenylphosphine oxide (Lucirin® TPO) and ethyl (2,4,6-trimethylbenzoyl)-phenyl phosphinate (Lucirin® TPO-L).

Since P-R substituted derivatives with R being a substituent bound via a carbon atom to the phosphors atom of the bisacylphosphine oxide structure generally provide a highly attractive application profile, there is still a need for liquid bisacylphosphine oxide photoinitiators of this structural type, which are not only liquid, but can also be prepared by a simple and inexpensive process.

It has now been found that such photoinitiators with a content of up to 100% of bisacylphosphine oxide components and a correspondingly high curing performance, which are liquid at room temperature, can be obtained by a simple and inexpensive process.

The invention relates to a liquid photoinitiator mixture comprising the components(a)
a compound of the formula (I)

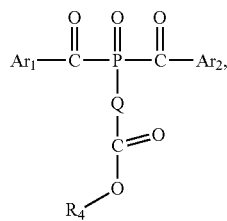

(I)

wherein $Ar_1$ and $Ar_2$ independently of each other are

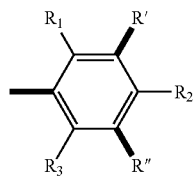

or naphthyl which is unsubstituted or substituted one or more times by $R_1$, $R_2$, $R_3$ or R';

$R_1$ and $R_3$ independently of each other are $C_1$-$C_4$alkyl, $C_1$-$C_4$alkoxy or halogen;

$R_2$ is hydrogen, $C_1$-$C_4$alkyl, halogen, $C_1$-$C_4$alkoxy or $C_2$-$C_{20}$alkoxy which is interrupted by one or more O;

Q is $C_1$-$C_4$alkylene;

$R_4$ is methyl or ethyl;

R' and R" independently of each other are hydrogen or PG-Y-R'''—X—;

PG is a polymerizable group or methyl or ethyl;

Y is a direct bond, O or S;

X is a direct bond, O or S;

R''' is a direct bond, $C_1$-$C_{20}$alkylene or $C_2$-$C_{20}$alkylene which is interrupted by one or more O;

(b) one or more compounds of the formula (II)

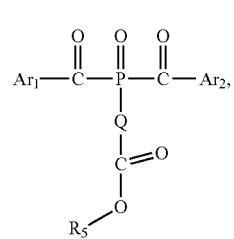

(II)

wherein $Ar_1$, $Ar_2$ and Q are as defined above, and $R_5$ is $C_3$-$C_{30}$alkyl which is unsubstituted or substituted by one or more of the groups selected from OH and

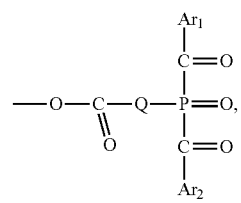

or $R_5$ is $C_2$-C28alkyl which is interrupted by one or more O or $C_3$-$C_8$cycloalkylene and which interrupted C3-C28alkyl is unsubstituted or substituted by one or more of the groups selected from OH and and

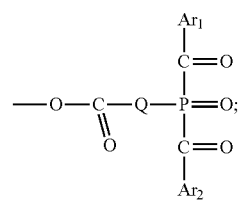

and
(c) optionally a compound of the formula (III)

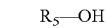 $R_5$—OH (III), wherein $R_5$ is as defined above.

$C_1$-$C_{20}$-alkyl is linear or branched and is, for example $C_1$-$C_{18}$-, $C_1$-$C_{14}$-, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_1$-$C_4$alkyl is linear or branched and is, for example, $C_1$-$C_3$-, $C_1$-$C_2$-, $C_2$-$C_4$-, $C_3$-$C_4$- or $C_2$-$C_3$alkyl. Examples are methyl, ethyl, propyl, isopropyl, n-butyl, sec-butyl, isobutyl and tert-butyl.

$C_3$-$C_{30}$-alkyl is linear or branched and is, for example, $C_3$-$C_{28}$-, $C_3$-$C_{24}$-, $C_3$-$C_{20}$-, $C_3$-$C_{18}$-, $C_3$-$C_{14}$-, $C_3$-$C_{12}$-, $C_3$-$C_8$-, $C_3$-$C_6$- or $C_3$-$C_4$alkyl. Examples are methyl, ethyl, propyl, iso-propyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl, icosyl etc.

$C_3$-$C_{30}$alkyl which is interrupted by one or more O is for example interrupted by 1-14, 1-12, 1-10, 1-8, 1-4, 1, 2 or 3 O.

$C_3$-$C_{30}$alkyl and $C_3$-$C_{28}$alkyl which is interrupted by one or more O which are substituted by one or more OH are for example substituted 1-5, 1-3 or one or two OH groups.

$C_1$-$C_4$alkoxy is linear or branched and is for example $C_1$-$C_3$-, $C_3$-$C_4$- or $C_2$-$C_3$alkoxy. Examples are methoxy, ethoxy, propoxy, isopropoxy, n-butyloxy, sec-butyloxy, isobutyloxy and tert-butyloxy.

$C_2$-$C_{10}$alkoxy interrupted by one or more O is for example interrupted 1-9, 1-7, 1-4 or once or twice by O. In case the groups are interrupted by more than one O, said O-atoms are separated from one another by at least one methylene group, i.e. the O-atoms are non-consecutive. Examples are the following structural units —O—$CH_2$—O—$CH_3$, —O—$CH_2CH_2$—O—$CH_2CH_3$, —O—[$CH_2CH_2$O]$_v$$CH_3$, with v=1-4, —O—($CH_2CH_2$O)$_4$$CH_2CH_3$, —O—$CH_2$—CH($CH_3$)—O—$CH_2$—$CH_2CH_3$, or —O—$CH_2$—CH($CH_3$)—O—$CH_2CH_3$.

Halogen is fluorine, chlorine, bromine and iodine, especially fluorine, chlorine and bromine, preferably fluorine and chlorine, most preferred chlorine.

$C_1$-$C_{20}$alkylene is linear or branched and is for example $C_1$-$C_{18}$-, $C_1$-$C_{14}$-, $C_1$-$C_{12}$-, $C_1$-$C_8$- , $C_1$-$C_6$- or $C_1$-$C_4$alkylene for example methylene, ethylene, propylene, 1-methylethylene 1,1-dimethylethylene, butylene, 1-methylpropylene, 2-methyl-propylene, pentylene, hexylene, heptylene, octylene, nonylene, decylene, dodecylene, tetradecylene, hexadecylene or octadecylene.

$C_2$-$C_{20}$alkylene which is interrupted by one or more O is linear or branched and is, for example, interrupted 1-9 times, for example 1-7 times or once or twice by O. The interrupting O atoms are non-successive This produces structural units such as, for example, —$CH_2$—O—$CH_2$—, —$CH_2CH_2$—O—$CH_2CH_2$—, —[$CH_2CH_2$O]$_y$—, —[$CH_2CH_2$O]$_y$—$CH_2$—, where y=1- 9, -($CH_2CH_2$O)$_7$—$CH_2CH_2$—, —$CH_2$—CH($CH_3$)—O—$CH_2$—CH($CH_3$)— or —$CH_2$—CH($CH_3$)—O-$CH_2$—$CH_2CH_2$—, etc.

A polymerizable group suitable in the present invention is for example —$CH_2$—CH=$CH_2$, —$CH_2$—C($CH_3$)=$CH_2$, —C($CH_3$)=$CH_2$, —CH=$CH_2$, -O-(CO)-C($CH_3$)=$CH_2$, —O—(CO)—CH=$CH_2$.

"photolatent catalyst" or "photoinitiator" refers to a compound, which upon irradiation with light, in particular with light of the wavelengths 150-800 nm, e.g. 200-800 or 200-600nm, provides an active catalyst or an active radical.

The terms "and/or" or "or/and" in the present context are meant to express that not only one of the defined alternatives (substituents) may be present, but also several of the defined alternatives (substituents) together, namely mixtures of different alternatives (substituents). The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, and process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is +1-10%.

$Ar_1$ and $Ar_2$ independently of each other are

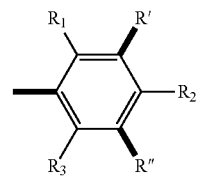

or naphthyl which is unsubstituted or substituted one or more times by $R_1$, $R_2$, $R_3$, R' or R". In particular $Ar_1$ and $Ar_2$ independently of each other are

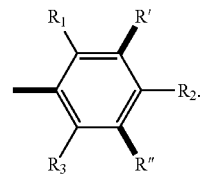

Preferably $Ar_1$ and $Ar_2$ are identical.

$R_1$ and $R_3$ independently of each other are $C_1$-$C_4$alkyl, $C_1$-$C_4$alkoxy or halogen. For example $R_1$ and $R_3$ independently of each other are $C_1$-$C_4$alkyl, in particular methyl, or $C_1$-$C_4$alkoxy, in particular methoxy. Preferably $R_1$ and $R_3$ independently of each other are $C_1$-$C_4$alkyl, in particular methyl. In preferred compounds $R_1$ and $R_3$ are identical.

$R_2$ is hydrogen, $C_1$-$C_4$alkyl, halogen, $C_1$-$C_4$alkoxy or $C_2$-$C_{20}$alkoxy which is interrupted by one or more O. $R_2$ in particular is hydrogen, $C_1$-$C_4$alkyl, in particular methyl, or $C_1$-$C_4$alkoxy, in particular methoxy. Preferably $R_2$ is hydrogen or $C_1$-$C_4$alkyl, in particular methyl. In preferred compounds $R_2$ is $C_1$-$C_4$alkyl, in particular methyl.

$R_2$ is for example identical with $R_1$ and $R_3$.

Q is for example $C_1$-$C_4$alkylene or $C_1$-$C_2$alkylene, in particular methylene.

$R_4$ is methyl or ethyl, in particular methyl.

R' and R" independently of each other are hydrogen or PG-Y-R'"—X—, in particular hydrogen. In preferred compounds R' and R" are identical.

PG is a polymerizable group or $C_1$-$C_{10}$-alkyl. PG as polymerizable group is preferably $CH_2$=CH—$CH_2$—, $CH_2=CH-$, $CH_2=CH-COO-$, $CH_2=C(CH_3)-COO-$, methyl or ethyl. PG for example is $C_1-C_{10}$alkyl, in particular methyl or ethyl. Or PG is for example $CH_2=CH-CH_2-$, $CH_2=CH-$, $CH_2=CH-COO-$ or $CH_2=C(CH_3)-COO-$.

Y is a direct bond, O or S. Y for example is a direct bond or O, or is a direct bond or S, or is O or S. Preferably Y is a direct bond or O, in particular a direct bond.

X is a direct bond, O or S. X for example is a direct bond or O, or is a direct bond or S, or is O or S. Preferably X is a direct bond or O, in particular a direct bond.

R''' is a direct bond, $C_1-C_{20}$alkylene or $C_2-C_{20}$alkylene which is interrupted by one or more O. For example R''' is $C_1-C_{20}$alkylene or $C_2-C_{20}$alkylene which is interrupted by one or more O, for example $C_1-C_{12}$alkylene or $C_2-C_{12}$alkylene interrupted by 1-6 O.

$R_5$ is for example $C_3-C_{30}$alkyl, or $C_2-C_{28}$alkyl which is interrupted by $C_3-C_8$cycloalkylene both of which are unsubstituted or substituted by

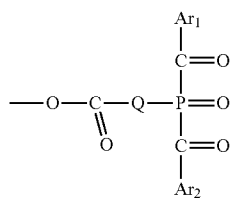

or OH. In particular $R_5$ is $C_3-C_{12}$alkyl, which is unsubstituted or substituted by

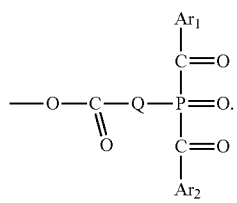

Preferably $R_5$ is unsubstituted $C_3-C_{12}$alkyl, especially octyl or nonyl, or is $C_3-C_{12}$alkyl, especially hexyl, which is substituted by

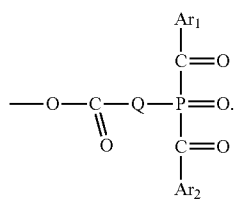

Component (b) for example comprises one or more different compounds of the formula (II). These one or more different compounds of the formula (II) for example bear different groups $R_5$.

One or more compounds of the formula (II) refer to m compounds of the formula (II), wherein m is for example 1-35, 5-35, 25-35, 1-25, 1-20, 1-10, 1-8, 1-6 or 1-3.

Of interest is a liquid photoinitiator mixture as defined above, wherein wherein 0.1-25% of component (a), 75-99.9% of component (b) and 0-25% of component (c) are present.

For example the mixture comprises 0.1-20% of component (a), 80-99.9% of component (b) and 0-19.9% of component (c).

Or the a liquid photoinitiator mixture comprises for example 1-25% of component (a), 75-99.0% of component (b) and 0-24% of component (c).

In another embodiment the liquid photoinitiator mixture comprises 2-10% of component (a), 90-98% of component (b) and 0-5% of component (c).

Preferred are liquid photoinitiator mixtures in which the amount of (a) and (c) is <10%, for example 1-9%, more preferred 5-9%.

Interesting is a liquid photoinitiator mixture as defined above, wherein $Ar_1$ and $Ar_2$ independently of one another other are

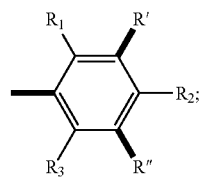

$R_1$ and $R_3$ independently of each other are $C_1-C_4$alkyl, $C_1-C_4$alkoxy or halogen;

$R_2$ is hydrogen, $C_1-C_4$alkyl, halogen, $C_1-C_4$alkoxy or $C_2-C_{20}$alkoxy which is interrupted by one or more O;

Q is $C_1-C_4$alkylene;

$R_4$ is methyl or ethyl;

R' and R" are hydrogen; and $R_5$ is $C_3-C_{30}$alkyl which is unsubstituted or substituted by one or more of the groups selected from OH and

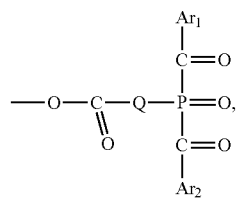

or $R_5$ is $C_2-C_{28}$alkyl which is interrupted by one or more $C_3-C_8$cycloalkylene and which interrupted $C_2-C_{28}$alkyl is unsubstituted or substituted by one or more of the groups selected from OH and

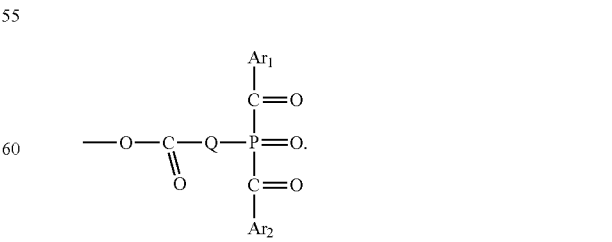

Further interesting is a liquid photoinitiator mixture as defined above, wherein $Ar_1$ and $Ar_2$ independently of one another other are

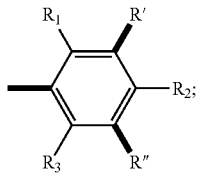

$R_1$ and $R_3$ independently of each other are $C_1$-$C_4$alkyl, in particular methyl, or $C_1$-$C_4$alkoxy, in particular methoxy;

$R_2$ is hydrogen, $C_1$-$C_4$alkyl, in particular methyl, or $C_1$-$C_4$alkoxy, in particular methoxy;

Q is $C_1$-$C_4$alkylene, in particular ethylene or methylene, preferably methylene;

$R_4$ is methyl or ethyl;

R' and R" are hydrogen; and $R_5$ is $C_3$-$C_{12}$alkyl which is unsubstituted or substituted by

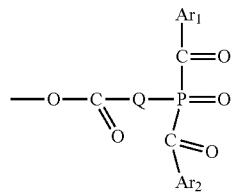

or OH, or $R_5$ is $C_2$-$C_{12}$alkyl which is interrupted by cyclohexylene or cyclopentylene and which interrupted $C_3$-$C_{12}$alkyl is substituted by

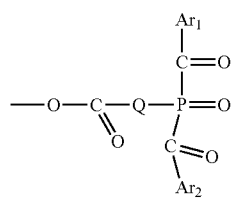

or OH.

Preferred is a liquid photoinitiator mixture as defined above, wherein wherein the compounds of the formula (I), (II) and (III)

$R_1$, $R_2$ and $R_3$ are $C_1$-$C_4$alkyl;

R' and R" are hydrogen;

Q is methylene, and $R_5$ is $C_3$-$C_{30}$alkyl which is unsubstituted or substituted by

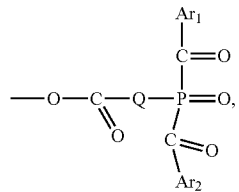

or $R_5$ is $C_2$-$C_{28}$alkyl which is interrupted by $C_3$-$C_8$cycloalkylene and which interrupted $C_3$-$C_{28}$alkyl is substituted by

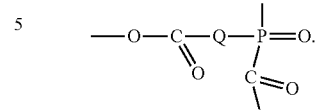

Interesting further is a liquid photoinitiator mixture as defined above, wherein the compounds of the formula (I), (II) and (III)

$R_1$, $R_2$ and $R_3$ are $C_1$-$C_4$alkyl, in particular methyl;

R' and R" are hydrogen;

Q is methylene, and $R_5$ is $C_3$-$C_{10}$alkyl, in particular octyl or nonyl, which is unsubstituted or $R_5$ is $C_3$-$C_8$alkyl, in particular hexyl, which is substituted by

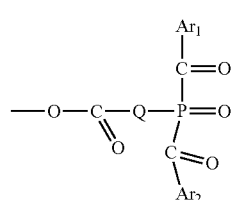

or OH, or $R_5$ is $C_2$-$C_6$alkyl which is interrupted by cyclohexylene and which interrupted $C_2$-$C_6$alkyl is substituted by

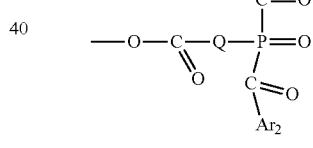

or OH.

Liquid mixtures of bisacylphosphine oxide photoinitiators of the current invention can be prepared via transesterification of a bisacylphosphine oxide of structure (I) with alcohols of structure (III) according to the following scheme:

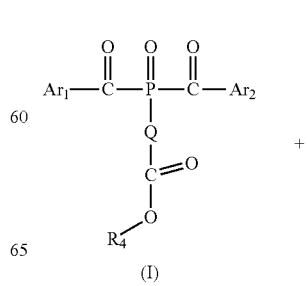

(I)

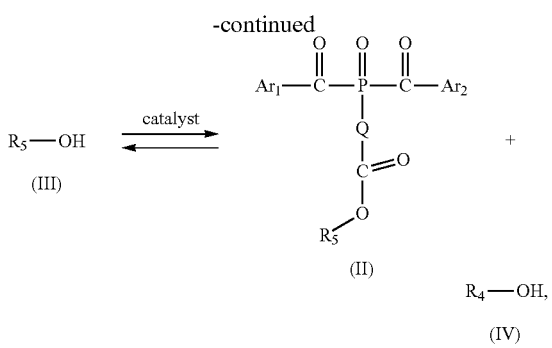

wherein $Ar_1$, $Ar_2$, $R_4$, $R_5$ and Q are as defined above.

For obtaining compounds of the formula II of a dimeric or multimeric structure, i.e. compounds of the formula II, wherein $R_5$ is alkylene which is substituted by one or more

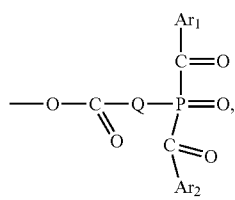

a corresponding poly-functional alcohol (III) is employed as the starting material.

When a poly-functional alcohol (III) is employed, all alcohol groups of the poly-functional alcohol (III) can be esterified in the transesterification product(s), or only part of the alcohol groups of the poly-functional alcohol (III) can be esterified. Most often a mixture of products with a different number of esterified alcohol groups of the poly-functional alcohol (III) are obtained. For example, if an n-functional poly-functional alcohol (III) is used, product mixtures containing mono-esterified poly-functional alcohol (III) to the n-times esterified poly-functional alcohol (III) are obtained. The person skilled in the art is aware of how to control degree of esterification to some extent e.g. by the transesterifaction conditions and by the stoichiometry of the alcohol groups in the poly-functional alcohol (III) and compound (I) used in the transesterification process.

Conditions for transesterification reactions are well known to the person skilled in the art and suitable conditions are for example reported in J. Otera, Chem. Rev. 1993, 93, 1449, or U. Schuchardt et al., J. Braz. Chem. Soc. 1998, 9, 199. The reaction can be performed neat using e.g. the alcohol component (III) as a solvent. Alternatively the reaction can be performed in a solution using a solvent that is inert under the transesterification conditions, such as for example pentane, hexane, heptane, cyclohexane, tetrahydrofuran, dichloromethane, benzene, toluene, xylene and the like, or mixtures thereof.

While the transesterification occurs essentially by mixing the reactants, addition of a catalyst is necessary in order to accelerate the process in order to achieve the required conversion within a useful time. Typical catalysts used are for example Bronsted acids, Lewis acids, Bronsted bases or Lewis bases. The catalyst is usually added in a small amount, typically in a range of 0.01-10 mol % based on the staring material. Examples of catalysts useful for transesterification reactions are dodecylbenzenesulfonic acid, tetraisopropyl orthotitanate, titanium diisopropoxide-bis-acetylacetoacetate, bis-2-(2-methoxyethoxy)ethoxy-titan-bis-acetylacetonate, butyltin tris(2-ethyl-hexanonate), dibutyltin oxide, dibutyltin dilaurate, dibutyltin diacetate, tin(II) 2-ethylhexanoate, lithium isopropylate, 1,3-dichloro-2,2,4,4-tetrabutyl-distannoxane, zirconium(IV)-n-propoxide, zirconium(IV)-n-butoxide, zirconium(IV)-acetylacetonate, zirconium(IV)-2-ethylhexanoate, magnesium acetylacetonate, vanadium(III) acetylacetonate, Fascat 4200, lithium methoxide, lithium acetate, potassium acetate, lithium carbonate, sodium carbonate, potassium carbonate, aluminum(III) acetate, aluminum(III) acetylacetonate, aluminium-tert-butoxide sodium hydroxide, lithium hydroxide, potassium hydrogencarbonate, potassium-tert.-butylate, 1,4-diazabicyclo[2.2.2]octan, (DABCO)1,5-diazabicyclo[4.3.0] non-5-ene (DBN), 1,8-diazabicyclo[5.4.0]undec-7-ene (DBU) 1,5,7-triazabicyclo[4.4.0]dec-5-ene (TBD) or thiaminnitrate.

Preferred catalysts are dibutyltin dilaurate. butyltin tris (2-ethyl-hexanonate), aluminum(III) acetylacetonate, zirconium(IV)-acetylacetonate or Fascat 4200 (Arkema Inc).

While the transesterification reaction occurs at room temperature or below, it is often advantageous to use higher temperatures in order to further accelerate the reaction. Thus the reaction temperature is usually in a range between 20° C. and 300° C., for example in a range between 30-200° C. and preferably in a range between 40-150° C. The upper limit of the useful temperature range is defined by the most volatile component, usually the alcohol (III) or the solvent.

Typically transesterification reactions are reversible processes producing an equilibrium mixture. The composition of the equilibrium mixture depends on the thermodynamical stability of the components. In order to promote the formation of the desired products several measures can be applied. The alcohol component (III) can be used in a large excess over the amount of the bisacylphosphine oxide (I), thereby promoting a shift of the equilibrium towards the products by the effect of the law of mass action. Removal of alcohol component (IV) by distillation under normal pressure or under vacuum is another means to shift the equilibrium towards the product side. It is also possible to use an entrainer to remove the alcohol (IV). Typical entrainers are for example solvents such as benzene, toluene, xylene, n-hexane, n-heptane, cyclohexane and the like. It is also possible to combine two or more of these means, such as e.g. using a large excess of alcohol (III) and distilling off the alcohol (IV) under vacuum. Still another possibility is using extractive conditions where a highly polar alcohol (e.g. $R_4=CH_3$) is removed due to its incompatibility with the non-polar reaction medium, for example if $CCl_4$ is used as solvent.

It is principally possible to bring the transesterification to 100% conversion, if suitable reaction conditions and reaction times are applied. Such reaction conditions and reaction times are, however, very laborious and costly and thus not practicable for an industrial process. Therefore the transesterification reaction is usually stopped before complete conversion is achieved, leaving a residual amount of starting material (I) in the reaction mixture. Depending on the reaction conditions, the amount of residual starting material may for example be in the range of 0.1- 25%.

This material can possibly be removed by a suitable procedure such as distillation, crystallization or any chromatographic purification technique. However, if the residual starting material does not negatively influence the properties and performance of the product, the latter may be used without any purification. This for example is the case for the liquid bisacylphosphine oxide photoinitiator mixtures of the present invention. Since the starting material (I) is a bisacylphosphine oxide photoinitiator, its presence will not significantly alter the curing performance of the product. If the starting material (I) is a solid compound with a limited solubility in the product mixture, its concentration has to be kept in a range where crystallization does not occur even upon prolonged storage at varying temperatures. Preferably the concentration of the starting material (I) in the product mixture is <25%, for example <15% and in particular <12%. If an excess of the alcohol (III) is used for the transesterification process, and/or if the conversion to the product (II) is not complete, the crude product mixture contains residual alcohol (III). This excess alcohol can be removed from the crude reaction mixture by distillation, possibly under vacuum. A liquid bisacylphosphine photoinitiator mixture free of alcohol (III) can thus be obtained. Depending on the volatility of the alcohol (III) an extensive, time-consuming and costly distillation is required for complete removal of the alcohol. Since small amounts of residual alcohol (III) do not significantly alter the curing performance of the liquid bisacyalphosphine oxide photoinitiator mixture, the presence of small amounts of alcohol (III) may even have a beneficial effect on the handling properties of the liquid bisacylphosphine oxide photoinitiator mixture by reducing the viscosity of the mixture. Therefore, a cost efficient technical process preferentially abstains from a complete removal of the alcohol (III). The residual alcohol content should, however, not exceed 25% in order to prevent a loss of curing efficiency by a dilution effect. Preferentially the amount of residual alcohol (III) is <15%, in particular <10%.

The transesterification process can be performed using a large excess of the alcohol (III) which in this case acts as solvent for the reaction and promotes a high conversion. The transesterification process can also be performed using small excess or even equimolar amounts of alcohol (III). Under these conditions it may be advantageous to use an inert solvent in order to achieve a useful initial viscosity of the reaction mixture. Preferred is the use of the solvent that can act as an entrainer for the alcohol (IV). Since large excesses of the alcohol (III) have to be removed after the reaction, reaction conditions using a relatively small amount of alcohol (III) are preferred for a technical process, since the costly distillation step is thus shortened or can be completely avoided. Preferred are reaction conditions using <5 mol equivalents of alcohol (III), for example <2 mol% and in particular <1.5 mol equivalent of alcohol (III).

Interesting are reaction conditions using a small excess of alcohol (III), which allow the use of the liquid bisacylphosphine oxide mixture as photoinitiator without the necessity for any distillation step to remove excess alcohol.

It is possible to produce a liquid bisacylphosphine oxide mixture containing only a small amount of alcohol (III) in the crude product, and to add afterwards a defined amount of alcohol (III) in order to achieve a product with a well defined content of alcohol and the corresponding viscosity. This approach allows for a better control of the final alcohol content and viscosity then a distillation process.

It is possible to remove the transesterification catalyst after the transesterification process, e.g. by washing or precipitating with a suitable complexing agent. However, if the catalyst is used in very low amounts, removal of the material may not be necessary and the residual catalyst is left in the reaction product.

Subject of the invention accordingly is a process for the preparation of a liquid photoinitiator mixture as defined in claim 1, by reacting a compound of the formula (I), as defined above with an alcohol of the formula (III)

$$R_5\text{—OH} \qquad (III),$$

wherein
R5 is as defined above,
in the presence of a catalyst and taking means to remove the alcohol of the formula
(IV) which is formed during the reaction

$$R_4\text{—OH} \qquad (IV),$$

wherein
$R_4$ is methyl or ethyl.

The synthesis of bisacylphosphine oxide of structure (I) is described in WO06/056541. Principally any of the ester-substituted compounds available by this process can be used as bisacylphosphine oxide starting material (I) in the transesterification reaction. The starting material should be a pure compound with a purity of at least >95%, for example >97% and in particular >98% in order to produce a liquid bisacylphosphine oxide photoinitiator of high purity according to the invention. The process as described in WO06/056541 is a multistep process producing a product that usually has a purity of <95% and hence requires a purification step. Purification is possible by any process known to the person skilled in the art, such as distillation, recrystallisation or any chromatographic technique. For a technical process, recrystallisation is the most convenlent, efficient and economical purification technique. Therefore a compound (I) that can easily be purified is preferred for use as starting material for the transesterification reaction. Compounds (I) possessing higher alkyl residues as $R_4$ defined for formula I above usually are obtained as sticky resins or lacquers that cannot be purified by crystallization. Compounds (I) possessing lower alkyl residues, as $R_4$ defined for formula I above, are obtained as solids that can be recrystallized for purification. Thus compounds (I) possessing alkyl residues $R_4$ that are lower than $R_5$ of formula II as defined above are used as starting material for the transesterification reaction. Preferred are the ethyl or methyl esters, which due to their relatively low solubility are most easily purified by recrystallisation. Moreover both derivatives are available according to the process described in WO06/056541 using cheap starting materials such as ethyl chloromethylacetate or methyl chloromethyl acetate.

Promoting a shift of the equilibrium of the transesterification reaction towards the product side requires that the alcohol (IV) formed during the reaction is removed by distillation or using an entrainer without concomitant removal of considerable amounts of the alcohol (III). This is best obtained if the boiling points of alcohol (II) and alcohol (IV) differ as much as possible. Since the alcohols (II) are relatively low volatile, best results are obtained if alcohol (IV) is a low-molecular, volatile compound such as ethanol or methanol. Therefore the use of compounds (I) with $R_4$ equals methyl or ethyl as starting material for the transesterification reaction is preferred. Most preferred is methyl.

Liquid bisacylphosphine oxide photoinitiators similar to those claimed in this invention can also be prepared by first transesterifying an alkyl 1-haloacetate (V), for example ethyl 1-chloroacetate, ethyl 1-bromoacetate, methyl 1-chloroacetate or methyl 1-bromoacetate with an alcohol of formula (III) to give the 1-haloacetate ester (VI). This ester is subsequently reacted to the bisacylphosphine oxide according to the method of WO06/056541. The reaction conditions for the transesterification reaction are as described before.

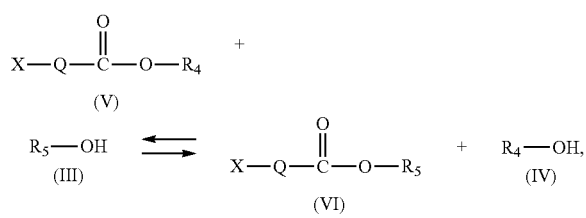

wherein Q, $R_4$ and $R_5$ are as defined above and X denotes a halogen, in particular Cl or Br. Due to the low volatility of the starting 1-haloacetate ester (V) and the alcohol (IV) it is possible to easily remove these compounds by distillation if required. Either the crude transesterification mixture or the purified 1-haloacetate (VI) is subsequently used as alkylating agent in the process described in WO06/056541.

Alcohols of the formula (III) which are useful for the transesterifcation reaction are linear or branched $C_3$-$C_{30}$alkyl alcohols which optionally are interrupted by oxygen or substituted by hydroxyl groups as defined above. The alcohols are for example primary, secondary or tertiary alcohols with primary alcohols being preferred. The alcohols are used as pure compounds or as technical fractions containing different isomers of the same chain lengths and/or different homologues of shorter and/or longer chain lengths. Although not pure compounds, these technical fractions are usually designated according to the chain lengths which make up for the major part of the alcohol mixture. When a pure alcohol is used for the transesterification reaction, the compound of structure (II) obtained by the reaction is a pure single compound. When a mixture of isomers or more specifically a technical fraction of alcohols is used for the transesterification reaction, the bisacylphosphine oxides of structure (II) consist of a mixture of isomeric and/or homologous compounds which may or may not reflect the composition of the starting alcohol mixture in $R_5$ depending on the relative reactivity of the different isomers and/or homologs present in the transesterification reaction.

Liquid mixtures of isomeric compounds have usually a lower tendency to crystallize or solidify than a single isomer of the same compound. Moreover liquid mixtures of isomeric compounds are often easier pourable then a single isomer of the same compound. Thus in view of preparing liquid bisacylphosphine oxide photoinitiator mixtures that have an excellent stability under varying storage conditions, such as varying temperature, and excellent handling properties such as the pouring ability, it is preferred to use mixtures of isomeric alcohols or more specifically technical fractions of isomeric and/or homologous alcohols.

Mixtures of isomeric and/or homologous alcohols can be prepared by mixing two or more pure isomers or homologues into a homogeneous liquid mixture. If necessary heat may be applied to promote the formation of a homologous liquid, especially if one or more of the pure compounds are of a solid or waxy consistence. Since isomeric and homologous alcohols are very compatible, the components can be mixed in any ratio in order to optimize the properties of the liquid bisacylphosphine oxide photoinitiator mixture according to the invention.

Mixtures of isomeric and/or homologous alcohols can also be obtained as technical mixtures which usually are a fraction from an industrial distillation process. As an example, a technical "isooctanol" fraction (Exxal™ 8, ExxonMobile Chemical) may contain as much as 30 alcohol components, including homologous $C_7$-, $C_8$-, $C_9$- and $C_{10}$- alcohol isomers. The amount of the individual alcohols typically is in the range of approximately 0.2-16%, and the sum of the $C_8$-isomers makes up for more than 85% of the total alcohol mixture.

As an example of a technical "isononanol" fraction, Nonanol N (BASF SE) contains more than 17 $C_9$-isomers, with the amount of individual $C_9$-alcohols typically being in the range of 0.3-21%.

In order to further expand the composition of the alcohol mixture it is further possible to use a combination of two or more technical fractions of isomeric and/or homologous alcohols; for example a mixture of a "isoheptanol" fraction with a "isotridecanol" fraction. Since all isomeric fractions are liquid, the components can easily be mixed in any ratio in order to optimize the properties of the liquid bisacylphosphine oxide photoinitiator mixture.

Examples of pure linear alkyl alcohols are for example Nacol® 6-98 (1-hexanol), Nacol® 8-98 or Nacol® 8-99 (1-octanol), Nacol® 10-97 or Nacol® 10-99 (1-decanol), Nacol® 12-96 or Nacol® 12-99 (1-dodecanol), Nacol® 14-95 or Nacol® 14-98 (1-tetradecanol), Nacol® 16-95 or Nacol® 16-98 (1-hexadecanol), all available from Sasol Limited.

Examples of pure branched alkyl alcohols are FINE OXOCOL 140 (isotetradecanol), FINE OXOCOL 160 (isopalmityl alcohol), FINE OXOCOL 180 (isostearyl alcohol), or FINE OXOCOL 2000 (isoecosanol), all available from Nissan Chemical) or 2-ethyl hexanol (Dow Chemical Company).

Examples of blends of linear alcohols are for example Nafol® 810D ($C_6$-$C_{12}$), Nafol® 10D ($C_8$-$C_{12}$), Nafol® 1012 ($C_8$-$C_{16}$), Nafol® 1214 ($C_{10}$-$C_{16}$), Nafol® 1214Z ($C_8$-$C_{18}$), Nafol® 1218 ($C_{10}$-$C_{20}$), Nafol® 1618 ($C_{12}$-$C_{22}$), Nafol® 1620 ($C_{12}$-$C_{24}$), Nafol® 20+ ($C_{16}$-$C_{26}$) or Nafol® 22+ ($C_{18}$-$C_{28}$), all available from Sasol Limited. Examples of industrially available fractions of branched primary alkyl alcohols are Exx-al™ 7 (isoheptanol), Exxal™ 8 (isooctanol), Exxal™ 9 (isononanol), Exxal™ 10 (iso-decanol), Exxal™ 11 (isoundecanol), Exxal™ 12 (isododecanol), or Exxal™ 13 (isotridecanol), all available from ExxonMobile Chemical, with "isoheptanol" "isooctanol", "isononanol", "isodecanol", "isoundecanol", "isododecanol" and "isotridecanol" meaning mixtures of various isomeric and homologous alcohols with the indicated alkyl chain length being the major fraction Other examples are Nonanol N (BASF SE), a mixture of isomeric nonyl alcohols, Oxocol 900 (Kyowa Hakko Chemical Co Inc, Ltd), isononyl alcohol mixture.

Examples of industrially "alkyl alcohol interrupted by oxygen" are for example Dowanol DE, Dowanol TE, Dowanol TMAT, Dowanol DM all available from Dow Chemicals. Tetraethylengylcol monoethyl ether or tetraethylengylcol monomethyl ether examples of alkyl alcohol interrupted by oxygen available as fine chemicals.

In accordance with the invention, the liquid photoinitiator mixture can be used as photoinitiator for the photopolymerization of ethylenically unsaturated compounds or of mixtures which comprise such compounds.

The invention therefore also relates to photopolymerizable compositions comprising
(A) at least one monomeric or oligomeric ethylenically unsaturated photopolymerizable compound and
(B) at least one liquid photoinitiator mixture as defined above.

The composition may comprise additionally to the components (A) and (B) at least one further photoinitiator (C) and/or other customary additives (D).

The unsaturated compounds (A) for example contain one or more olefinic double bonds. They are of low molecular weight (monomeric) or higher molecular weight (oligomeric).

Examples of monomers containing a double bond are (meth)acrylic acid and salts thereof, (meth)acrylic acid esters, e.g. alkyl esters such as methyl, ethyl, 2-chloroethyl, N-dimethylaminoethyl, n-butyl, isobutyl, pentyl, hexyl, cyclohexyl, 2-ethylhexyl, octyl, isobornyl [2-exobornyl] ester, phenyl, benzyl and o-, m- and p-hydroxyphenyl ester, hydroxyalkyl esters, e.g. 2-hydroxyethyl, 2-hydroxypropyl, 4-hydroxybutyl, 3,4-dihydroxybutyl or glycerol [1,2,3-propanetriol] ester, epoxyalkyl esters, e.g. glycidyl, 2,3-epoxybutyl, 3,4-epoxybutyl, 2,3-epoxycyclohexyl, 10,11-epoxyundecyl ester, (meth)acrylamides, N-substituted (meth) acrylamides, e.g. N-methylolacrylamide, N-methylolmethacrylamide, N-ethylacrylamide, N-ethylmethacrylamide, N-hexylacryl-amide, N-hexylmethacrylamide, N-cyclohexylacrylamide, N-cyclohexylmethacrylamide, N-hydroxyethylacrylamide, N-phenylacrylamide, N-phenylmethacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide and N-(4-hydroxyphenyl)methacrylamide, IBMAA (N-isobutoxymethylacrylamide), (meth)acrylonitriles, unsaturated acid anhydrides such as itaconic anhydride, maleic anhydride, 2,3-dimethylmaleic anhydride, 2-chloromaleic anhydride, unsaturated esters such as maleic acid esters, phthalic acid esters, itaconic acid esters [methylenesuccinic acid esters], styrenes such as methylstyrene, chlorome-thylstyrene and o-, m- and p-hydroxystyrene, divinylbenzene, vinyl ethers such as iso-butyl vinyl ether, ethyl vinyl ether, 2-chloroethyl vinyl ether, hydroxyethyl vinyl ether, propyl vinyl ether, butyl vinyl ether, isobutyl vinyl ether, octyl vinyl ether and phenyl vinyl ether, vinyl and allyl esters such as vinyl acetate, vinyl acrylate, vinyl chloroacetate, vinyl butyrate and vinyl benzoate, divinyl succinate, diallyl phthalate, triallyl phosphate, vinyl chloride and vinylidene chloride, isocyanurates such as triallyl isocyanurate and tris(2-acryloylethyl) isocyanurate, N-vinyl-heterocyclic compounds such as N-vinyl pyrrolidones or substituted N-vinylpyrrolidones, N-vinylcaprolactam or substituted N-vinylcaprolactams, N-vinylcarbazole, N-vinylpyridine.

Further examples of suitable esters are: diacrylate esters such as 1,6-hexanediol diacrylate (HDDA), ethylene glycol diacrylate, propylene glycol diacrylate, dipropylene glycol diacrylate, tripropylene glycol diacrylate, neopentyl glycol diacrylate, hexamethylene glycol diacrylate and bisphenol A diacrylate, trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having molecular weights of from 200 to 1500, or mixtures thereof. Frequently also used are acrylic acid esters of alkoxylated alcohols, e.g. glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate. Examples of higher-molecular-weight unsaturated compounds (oligomers, prepolymers) are esters of ethylenically unsaturated mono- or poly-functional carboxylic acids and polyols or polyepoxides, and polymers having ethylenically unsaturated groups in the chain or in side groups such as, for example, unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more of such polymers.

Examples of suitable mono- or poly-functional unsaturated carboxylic acids are acrylic acid, methacrylic acid, crotonic acid, cinnamic acid, maleic acid, fumaric acid, itaconic acid, unsaturated fatty acids such as linolenic acid or oleic acid. Acrylic and methacrylic acid are preferred.

However, saturated di- or poly-carboxylic acids in admixture with unsaturated carboxylic acids may also be used. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc.

As polyols, aromatic and especially aliphatic and cycloaliphatic polyols are suitable. Examples of aromatic polyols are hydroquinone, 4,4'-dihydroxydiphenyl, 2,2-di(4-hydroxyphenyl)propane, and also novolaks and resols. Examples of polyepoxides are those based on the mentioned polyols, especially aromatic polyols and epichlorohydrin. Also suitable as polyols are polymers and copolymers that contain hydroxyl groups in the polymer chain or in side groups such as, for example, polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethyl-cyclohexane, glycerol, tris(β-hydroxyethypamine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids. Examples of polyurethanes are those composed of saturated diisocyanates and unsaturated diols or unsaturated diisocyanates and saturated diols.

Preference is given to methacrylated epoxy esters, methacrylated polyesters, polyesters carrying vinyl groups, methacrylated polyurethanes, methacrylated polyethers and polyols.

Suitable components (A) are also acrylates which have been modified by reaction with primary or secondary amines, as described, for example, in U.S. Pat. No.3,844, 916, in EP280222, in U.S. Pat. Nos. 5,482,649 or in 5,734, 002. Such amine-modified acrylates are also termed amine acrylates. Amine acrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley and GENOM ER 5275 from Rahn. Some acrylate binders expecially designed for low extractables and odour applications can also be used in the formulation. Such resins are commercially available for example under the tradename Ebecryl LEO resins.

Furthermore, cationically UV-curable compositions may be used as part of component (A) for hybrid cationic/radical UV-curing. Such systems typically comprise aliphatic and/or aromatic epoxides, at least one polyol or polyvinyl polyol or oxetane and also at least one photoinitiator that generates cations. The said epoxides, polyols and polyvinyl polyols are known in the art and commercially available. The customarily used photoinitiators are iodonium and sulfonium salts as described, for example, in U.S. Pat. No. 6,306,555. In addition, ethylenically unsaturated compounds may be added to the said cationically UV-curable compositionsIt is also possible to add solvents or water to the compositions used in the process according to the invention. Suitable solvents are solvents which are known to the person skilled in the art and are conventional especially in surface-coating technology. Examples are various organic solvents such as, for example, ketones, e.g. methyl ethyl ketone, cyclohexanone; aromatic hydrocarbons, e.g. toluene, xylene or tetramethylbenzene; glycol ethers, e.g. diethylene glycol monoethyl ether, dipropylene glycol diethyl ether; esters, e.g. ethyl acetate; aliphatic hydrocarbons, e.g. hexane, octane, decane; or petroleum solvents, e.g. petroleum ether.

The invention relates also to compositions comprising, as component (A), at least one ethylenically unsaturated photopolymerisable compound dissolved or emulsified in water.

Such radiation curable aqueous prepolymers can aso be aqueous prepolymer emulsions. Examples are products like Laromer PE 22WN or Laromer PE 55WN. Such radiation-curable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The radiation-curable prepolymer or prepolymer mixture is present in concentrations of, for example, from 95 to 20% by weight, especially from 70 to 40% by weight. The sum of the indicated percentages for water and prepolymer in those compositions is in each case 100; auxiliaries and additives, which are present in varying amounts depending on the intended use, are in addition thereto.

The radiation-curable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use pre-polymers having higher molecular weights also come into consideration. Used are, for example, polyesters containing polymerisable C—C double bonds and having an acid number of at most 10, polyethers containing polymerisable C—C double bonds, hydroxyl-group-containing reaction products of a polyepoxide containing at least two epoxide groups per molecule with at least one α,β-ethylenically unsaturated carboxylic acid, polyurethane (meth)acrylates and also acrylic copolymers containing α,β-ethylenically unsaturated acrylic radicals as described, for example, in EP012339. Mixtures of those prepolymers may also be used. Also suitable are, for example, the polymerisable prepolymers described in EP033896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on particular (meth) acrylic acid alkyl ester polymerisation products are described in EPO41125; suitable water-dispersible, radiation-curable prepolymers obtained from urethane acrylates are to be found in, for example, DE2936039.

The photopolymerisable compounds (A) are used singly or in any desired mixture. Component (A) may also comprise binders, that being especially advantageous when the photopolymerisable compounds are liquid or viscous substances. The amount of the binder may be, for example, from 5 to 95% by weight, preferably from 10 to 90% by weight and especially from 40 to 90% by weight, based on the total solid material. The binder is selected according to the field of use and the properties required therefor such as, for example, developability in aqueous and organic solvent systems, adhesion to substrates and sensitivity to oxygen.

Suitable binders are, for example, polymers having molecular weights of about 5 000-2 000 000, preferably 10 000 - 1 000 000. Examples are: homo- and co-polymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, e.g. cellulose acetate, cellulose acetate butyrate, methylcellulose, ethylcellulose; polyvinyl butyral, polyvinyl formal, cyclised rubber, polyethers, e.g. polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers, e.g. polycaprolactam and poly(hexamethylene adipamide), polyesters, e.g. poly(ethylene glycol terephthalate) and poly(hexamethylene glycol succinate). The unsaturated compounds may also be used in admixture with non-photopolymerisable film-forming components. The latter are, for example, physically drying polymers or solutions thereof in organic solvents, e.g. nitrocellulose or cellulose acetobutyrate, but may also be chemically or thermally curable resins, e.g. polyisocyanates, polyepoxides or melamine resins. Melamine resins are to be understood as including not only condensation products of melamine (=1,3,5-triazine-2,4,6-triamine) but also those of melamine derivatives. In general, the binder is a film-forming binder based on a thermoplastic or thermocurable resin, mainly a thermocurable resin. Examples thereof are alkyd, acrylic, polyester, phenol, melamine, epoxy and polyurethane resins and mixtures thereof. The concomitant use of thermally curable resins is of importance for use in so-called hybrid systems, which are both photopolymerised and also thermally crosslinked.

Component (A) may also comprise film-forming binders based on a thermoplastic or thermocurable resin, mainly a thermocurable resin. Examples thereof are alkyd, acrylic, polyester, phenol, melamine, epoxy and polyurethane resins and mixtures thereof. Examples thereof are described in, for example, Ullmann's Encyclopedia of Industrial Chemistry, 5th Ed., Vol. A18, pp. 368-426, VCH, Weinheim 1991. The binder may be a binder that fully cures at cold or hot temperatures, for which the addition of a curing catalyst may be advantageous. Suitable catalysts which accelerate full curing of the binder are described in, for example, Ullmann's Encyclopedia of Industrial Chemistry, Vol. A18, p. 469, VCH Verlagsgesellschaft, Weinheim 1991.

WO99/03930; WO2000/010974 and WO2000/020517 describe maleimide-modified binders. Maleimide-modified binders of that kind may likewise be present in the photocurable composition of the present invention.

Examples of binders are:

1. surface-coatings based on cold- or hot-crosslinkable alkyd, acrylate, polyester, epoxy or melamine resins or mixtures of such resins, optionally with the addition of a curing catalyst;
2. two-component polyurethane surface-coating compositions based on hydroxyl-group-containing acrylate, polyester or polyether resins and aliphatic or aromatic isocyanates, isocyanurates or polyisocyanates;
3. two-component polyurethane surface-coating compositions based on thiol-group-containing acrylate, polyester or polyether resins and aliphatic or aromatic isocyanates, isocyanurates or polyisocyanates;
4. single-component polyurethane surface-coating compositions based on blocked isocyanates, isocyanurates or polyisocyanates, which are unblocked during stoving; optionally, the addition of melamine resins is also possible;
5. single-component polyurethane surface-coating compositions based on aliphatic or aromatic urethanes or polyurethanes and hydroxyl-group-containing acrylate, polyester or polyether resins;
6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;
7. two-component surface-coating compositions based on (poly)ketimines and aliphatic or aromatic isocyanates, isocyanurates or polyisocyanates;
8. two-component surface-coating compositions based on (poly)ketimines and an unsaturated acrylate resin or a polyacetoacetate resin or a methacrylamidoglycolate methyl ester;
9. two-component surface-coating compositions based on carboxyl- or amino-group-containing polyacrylates and polyepoxides;
10. two-component surface-coating compositions based on anhydride-group-containing acrylate resins and a polyhydroxy or polyamino component;
11. two-component surface-coating compositions based on acrylate-containing anhydrides and polyepoxides;
12. two-component surface-coating compositions based on (poly)oxazolines and anhydride-group-containing acrylate resins or unsaturated acrylate resins or aliphatic or aromatic isocyanates, isocyanurates or polyisocyanates;
13. two-component surface-coating compositions based on unsaturated (poly)acrylates and (poly)malonates;
14. thermoplastic polyacrylate surface-coating compositions based on thermoplastic acrylate resins or extrinsically crosslinking acrylate resins, in combination with etherified melamine resins;
15. surface-coating systems, especially clearcoats, based on malonate-blocked isocyanates with melamine resins (e.g. hexamethoxymethyl melamine) as crosslinkers (acid-catalysed);
16. UV-curable systems based on oligomeric urethane acrylates and/or acylate acrylates, optionally with the addition of other oligomers or monomers;
17. dual-cure systems, which are first cured thermally and then UV-cured, or vice versa, wherein constituents of the surface-coating composition contain double bonds which can be made to react by UV light and photoinitiators and/or by electron-beam curing.

Both 1-component (1C) and 2-component (2C) systems may be used as binder. Examples of such systems are described in Ullmann's Encyclopedia of Industrial Chemistry, Vol. A18, Paints and Coatings, page 404-407, VCH Verlagsgesellschaft mbH, Weinheim (1991).

The composition can be optimised by specifically modifying the formulation, e.g. by varying the binder/crosslinker ratio. The person skilled in the art of coating or ink technology will be familiar with such measures.

The photopolymerizable composition of the invention for example additionally comprises a binder polymer (e), in particular a copolymer of methacrylate and methacrylic acid.

In addition to the photoinitiator, the photopolymerisable mixtures may comprise various additives (D). Examples thereof are thermal inhibitors, which are intended to prevent premature polymerisation, e.g. 2,2,6,6-tetramethyl-4-hydroxy-piperidin-1-oxyl (4-hydroxy-TEMPO) and derivatives thereof, e.g. bis(2,2,6,6-tetramethylpiperidin-1-oxyl-4-yl)-decanedioate or polyalkyl-piperidin-N-oxyl radicals, 3-aryl-benzofuran-2-one and derivatives thereof, e.g. 5,7-di-tert-butyl-3-phenyl-3H-benzofuran-2-one (as described in, for example, WO01/42313), hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS). Such compounds are widely known to the person skilled in the art.

Examples of such UV absorbers and light stabilisers are disclosed in WO04/074328, page 12, line 9 to page 14, line 23, said disclosure hereby is incorporated by reference. Further, additives that are customary in the art such as, for example, antistatics, flow improvers and adhesion promoters may be used.

In accordance with the invention, if the formulation comprises binder, thermal drying or curing catalysts may additionally be added to the formulation as additional additives (D). Possible drying catalysts, or thermal curing catalysts, are, for example, organic metal compounds, amines or/and phosphines. Organic metal compounds are, for example, metal carboxylates, especially those of the metals Pb, Mn, Hf, Co, Zn, Zr or Cu, or metal chelates, especially those of the metals Hf, Al, Ti or Zr, or organometal compounds, such as e.g. organotin compounds. Examples of metal carboxylates are the stearates of Pb, Mn or Zn, the octoates of Co, Zn or Cu, the naphthenates of Mn and Co or the corresponding linoleates or tallates (tall oil, which contains rosin acids, oleic and linoleic acids). Examples of metal chelates are the aluminium, titanium or zirconium chelates of acetyl acetone, ethylacetyl acetate, salicylaldehyde, salicylaldoxime, o-hydroxyacetophenone or ethyl-trifluoroacetyl acetate and the alkoxides of those metals. Examples of organotin compounds are dibutyltin oxide, dibutyltin dilaurate and dibutyltin dioctoate. Examples of amines are especially tertiary amines such as, for example, tributylamine, triethanolamine, N-methyldiethanolamine, N-dimethylethanolamine, N-ethylmorpholine, N-methylmorpholine and diazabicyclooctane (triethylenediamine) and the salts thereof. Further examples are quaternary ammonium salts, such as e.g. trimethylbenzylammonium chloride. It is also possible to use phosphines such as, for example, triphenylphosphine, as curing catalysts. Suitable catalysts are also described in, for example, J. Bielemann, Lackadditive, Wiley-VCH Verlag GmbH, Weinheim, 1998, pages 244-247. Examples are carboxylic acids such as, for example, p-toluenesulfonic acid, dodecylbenzenesulfonic acid, dinonylnaphthalenesulfonic acid and dinonylnaphthalenedisulfonic acid. There may also be used, for example, latent or blocked sulfonic acids, it being possible for the blocking of the acid to be ionic or non-ionic.

Such catalysts are used in concentrations customary in the art and known to the skilled person.

In order to accelerate photopolymerisation, amines may be added as further additives (D), especially tertiary amines, e.g. tributylamine, triethanolamine, p-dimethylaminobenzoic acid ethyl ester, Michler's ketone, N-methyl-diethanolamine, N-dimethylethanolamine, N-ethylmorpholine, N-methylmorpholine, diazabicyclooctane (triethylenediamine), 18-diazabicyclo[5.4.0]undec-7-ene (DBU), 1,5-diazabicyclo[4.3.0]non-5-ene (DBN) and salts thereof. Further examples are quaternary ammonium salts, e.g. trimethylbenzylammonium chloride. The action of the amines may be reinforced by adding aromatic ketones of the benzophenone type. Amines that are suitable as oxygen capture agents are, for example, N,N-dialkylanilines as described in EP339841. Further accelerators, coinitiators and auto-oxidisers are thiols, thioethers, disulfides and phosphines as described in, for example, EP438123 and GB2180358. It is also possible for chain transfer reagents customary in the art to be added to the compositions according to the invention. Examples are mercaptans, amines and benzothiazole.

Photopolymerisation can also be accelerated by addition, as further additives (D), of photosensitisers, which shift or broaden the spectral sensitivity. These include especially aromatic carbonyl compounds such as, for example, benzophenone derivatives, thioxanthone derivatives, including especially isopropyl thioxanthone, anthraquinone derivatives and 3-acylcoumarin derivatives, terphenyls, styryl ketones, and 3-(aroylmethylene)-thiazolines, camphorquinone and also eosin, rhodamine and erythrosine dyes. The amines mentioned above, for example, may also be regarded as photosensitisers. Examples of suitable sensitizer compounds (D) are disclosed in WO06/008251, page 36, line 30 to page 38, line 8, the disclosure of which is hereby incorporated by reference.

The curing process, especially of pigmented (e.g. pigmented with titanium dioxide) compositions, can also be assisted by adding an additional additive (D) which under thermal conditions is a free-radical-forming component, for example an azo compound, e.g. 2,2'-azobis(4-methoxy-2,4-dimethylvaleronitrile), a triazene, a diazo sulfide, a pentazadiene or a peroxy compound such as a hydroperoxide or peroxycarbonate, e.g. tert-butyl hydroperoxide as described in, for example, EP245639.

Further customary additives (D) are—depending on the intended use—fluorescent whitening agents, fillers, e.g. kaolin, talc, barite, gypsum, chalk or silicate-type fillers, wetting agents or flow improvers.

For curing thick and pigmented coatings, the addition of glass microspheres or powdered glass fibres is suitable, as described in, for example, U.S. Pat. No. 5013768.

The formulations may also comprise dyes and/or white or coloured pigments [as further additve (D)]. Depending on the intended use, both inorganic and organic pigments may be used. Such additives will be known to the person skilled in the art; a few examples are titanium dioxide pigments, e.g. of the rutile or anatase type, carbon black, zinc oxide, e.g. zinc white, iron oxides, e.g. iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments.

The pigments may be used in the formulations singly or in admixture.

The pigments are added to the formulations, in accordance with the intended use, in amounts customary in the art, for example in an amount of from 1 to 60% by weight, or from 10 to 30% by weight, based on the total mass.

The formulations may also comprise, for example, organic dyes from a very wide variety of classes. Examples are azo dyes, methine dyes, anthraquinone dyes or metal complex dyes. Customary concentrations are, for example, from 0.1 to 20%, especially from 1 to 5%, based on the total mass.

Selection of the additives is based on the particular field of use of the photopolymerizable composition and the properties desired in that field.

Subject of the invention also is a photopolymerizable composition as described above as further additive (D) comprising a pigment or dye or a mixture of pigments or dyes. The additives (D) described hereinbefore are customary in the art and are accordingly used in amounts customary in the art.

It is, of course, possible to use mixtures of the compound of the invention with one or more known photoinitiators (C), for example mixtures with camphor quinone; benzophenone, benzophenone derivatives, such as 2,4,6-trimethylbenzophenone, 2-methylbenzophenone, 3-methylbenzophenone, 4-methyl benzophenone, 2-methoxycarbonylbenzophenone 4,4'-bis(chloromethyl) benzophenone, 4-chlorobenzophenone, 4-phenylbenzophenone, 3,3'-dimethyl-4-methoxy-benzophenone, [4-(4-methylphenyl-thio)phenyl]-phenylmethanone, methyl-2-benzoyl benzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methylethane, 1-(4-isopropyl benzoyl)-1-hydroxy-1-methylethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)-phenoxy]-phenyl}-2-methyl-propan-1-one; oligomeric α-hydroxy ketones; dialkoxyacetophenones, α-hydroxy- or α-amino-acetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methyl-benzyl)-1-dimethylaminopropane, (4-(2-hydroxyethyl) aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxophenyl-acetic acid 2-(2-hydroxy-ethoxy)-ethyl ester, dimeric phenylglyoxalic esters, e.g. oxo-phenyl-acetic acid 1-methyl-2-2-(2-oxo-2-phenyl-acetoxy)-propoxyFethyl ester; oximeesters, e.g. 1,2-octanedione 1-[4-(phenylthio) phenyl]-2-(O-benzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), or for example a combination of oxime esters with α-amino ketones, e.g. a combination of (4-morpholinobenzoyl)-1-benzyl-1-dimethylaminopropane with [4-(2-methylphenylcarboxy)phenyl]-bis[4-(O-acetyloximine)phenyl] amine; peresters, e,g. benzophenone tetracarboxylic peresters as described for example in EP126541, monoacyl phosphine oxides, e.g. (2,4,6-trimethylbenzoyl)diphenylphosphine oxide, ethyl (2,4,6-trimethylbenzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxyphenyl)-4,6-bis-trichloromethyl-[1,3,5]triazine, 2-methyl-4,6-bis-trichloromethyl-[1,3,5]triazine, hexaarylbisimidazole/coinitiator systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrrylphenyptitanium. Further, borate compounds can be used as coinitiators.

Many of said additional photoinitiators (C) are commercially available, for example under the tradenames Darocur® and Irgacure® from BASF SE or Esacure® from Lamberti.

Compounds of the invention are for example used in combination with other photoinitiators (C) that provide complementary application characteristics, thereby improving the overall performance of the initiating system. For many applications addition of one photoinitiator (C) gives good results. For other uses addition of two or even more additional photoinitiators (C) may be recommendable to achieve optimum results.

If mixtures of the compounds of the invention with other photoinitiators (C) are used, the compounds can be added individually to the formulation. Alternatively it is possible to mix the compounds of the invention with one or more other photoinitiators (C) before the compounds are added to the formulation. Two or more of the photoinitiators (C) to be mixed with the compounds of the invention may in turn be used as a corresponding blend. Several such blends are commercially available (for example Irgacure®500 or Irgacure®2022). Blending of compounds of the invention with other photoinitiators (C) before the addition to the formulation can be advantageous in order to improve handling properties and the ease of incorporation as compared to using the individual compounds. Since the compounds of the invention are liquids, the scope of possible blends is large, especially when one or more photoinitiators (C) are also liquid.

Accordingly subject of the invention is a liquid photoinitiator mixture as described above additionally comprising at least one further photoinitiator (C). Especially preferred are blends where one or more of the other photoinitiators (C) are also liquids.

If the blend consists of a liquid photoinitiator as described above and one other liquid or solid photoinitiator (C), the two components can be mixed in a ratio of 99.9-0.1% of the liquid photoinitiator and 0.1-99.9% of the photoinitiator (C).

If the blend consists of a liquid photoinitiator as described above and two or more other liquid or solid photoinitiators (C), the three or more components can be used in any ratio. Preferred are ratios that provide a liquid blend at ambient temperature.

Subject of the invention also is a photopolymerizable composition as described above, wherein the additional photoinitiator (C) is selected from the group consisting of alpha-hydroxy ketones, benzophenone, substituted benzophenone compounds, benzildimethylketal, phenylglyoxylate compounds and alpha-aminio ketone compounds.

For example the additional photoinitiator (C) is selected from the group consisting of benzophenone, 2,4,6-trimethylbenzophenone, 2-methyl benzophenone, 3-methylbenzophenone, 4-methyl benzophenone, 2-methoxycarbonylbenzophenone 4,4'-bis(chloromethyl)benzophenone, 4-chlorobenzophenone, 4-phenyl benzophenone, 3,3'-dimethyl-4-methoxy-benzophenone, [4-(4-methylphenylthio) phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone, benzildimethylketal, acetophenone, 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl ]-phenyl}-2-methyl-propan-1-one; 2-hydroxy-1-{4-[4-(2-hydroxy-2-methyl-propionyl)-phenoxy]-phenyl}-2-methyl-propan-1-one, (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl)aminobenzoyl)-1-benzyl-1-dimethylaminopropane), (3,4-dimethoxybenzoyl)-1-benzyl- 1-dimethylaminopropane, methyl α-oxo benzeneacetate, oxo-phenyl-acetic acid 2-(2-hydroxyethoxy)-ethyl ester and oxo-phenyl-acetic acid 1-methyl-2-[2-(2-oxo-2-phenyl-acetoxy)-propoxy]ethyl ester, Esacure®KI P150, Esacure®160.

Interesting examples of additional photoinitiators (C) are selected from the group consisting of 2-hydroxy-2-methyl-1-phenyl-propanone, 1-hydroxy-cyclohexyl-phenyl-ketone, 2-hydroxy-1-{4-[4-(2-hydroxy-2-methyl-propionyl)-benzyl]-phenyl}-2-methyl-propan-1-one, Esacure KIP® 150, methyl α-oxo benzeneacetate, oxo-phenyl-acetic acid 2-(2-hydroxy-ethoxy)-ethyl ester and oxo-phenyl-acetic acid 1-methyl-2-[2-(2-oxo-2-phenyl-acetoxy)-propoxy]-ethyl ester.

In particular preferred additional photoinitiators (C) are selected from the group consisting of 2-hydroxy-2-methyl-1-phenyl-propanone, 2-hydroxy-2-methyl-1-(3-[3hydroxyl-methyl]-phenyl)-1-propanone, 1,1'-[oxybis(methylene-3,1-phenylene)]bis[2-hydroxy-2-methyl-1-propanone, 1-hydroxy-cyclohexyl-phenyl-ketone, 2-hydroxy-1-{4-[4-(2-hydroxy-2-methyl-propionyl)-benzyl]-phenyl}-2-methyl-propan-1-one, poly{2-hydoxy-2-methyl-1-[4-(1-methylvinyl)phenyl]propanone} (Esacure® KIP 150), 2-hydroxy-1-{4-[4-(2-hydroxy-2-methyl-propanoyl)phenoxy]-phenyl}-2-methyl-propan-1-one (Esacure® 160), 1-[4-(4-benzoylphenylsulfanyl)phenyl]-2-methyl-2-[(4-methylphenyl)sulfonyl]propan-1-one (Esacure® 1001), methyl phenylglyoxalate (Darocur® MBF), oxyphenylacetic acid 2-[2-oxo-2-phenylacetoxy)-ethoxy]-ethyl ester (Irgacure® 754), 2,4,6-trimethylbenzoylethoxyphenylphosphine oxide (Lucirin® TPO-L), bis(2,4,6-trimethyl-benzoyl)-phenyl phosphine oxide, Irgacure®819, diphenyl(2,4,6-trimethylbenzoyl)phosphine oxide (Lucirin® TPO), 4-(4-methylphenylthio)benzophenone, diester of carboxymethoxy-benzophenone and poly(tetramethylene glycol 250), isopropylthioxanthone, 1-chloro4-propoxy-thioxanthone, 2,4-diethyl-9H-thioxanthen-9-one, diester of 2-carboxymethoxy-thioxanthone and poly(tetramethyleneglycol 250), 2-methyl-1-(4-methylsulfanylphenyl)-2-morpholino-propan-1-one (Irgacure® 907), 2-benzyl-2-(dimethylamino)-1-(4-morpholinophenyl)-1-butanone (Irgacure® 369), 2-(4-methylbenzyl)-2-(dimethylamino)-1-(4-morpholinophenyl)butan-1-one (Irgacure® 379), and polyethyleneglycol-di(β-4-[4-(2-dimethylamino-2-benzyl)butaonylphenyl] piperazine)propionate.

The photopolymerizable composition as described above for example comprises 0.05 to 15% by weight, preferably 0.1 to 5% by weight, of the photoinitiator (B) or the photoinitiators (B)+(C), based on the composition.

The compositions according to the invention can be used for various purposes, for example in overprint coatings, as printing ink, e.g. screen printing ink, ink for offset- or flexo printing, inkjet ink, ink for sheet-fed printing, electrophotography ink, intaglio ink, as clearcoats, white coats or colour-pigmented coats, e.g. for wood or metal, as powder coatings, as paints, inter alia for paper, wood, metal or plastics, as daylight-curable paints for marking structures and roads, paints for buildings, constructions, vehicles, aircraft, etc., for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by curing in the mass (UV curing in transparent moulds) or according to the stereolithography process, as described in, for example, U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical apparatus, aids or implants. The compositions can also be used for the preparation of gels having thermotropic properties. Such gels are described in, for example, DE19700064 and EP678534.

Photocuring further is of great importance for printing applications, since the drying time of the ink is a critical factor for the production rate of graphic products, and should be in the order of fractions of seconds. UV-curable inks are particularly important for screen printing, offset inks, ink-jet inks, flexographic printing inks, intaglio inks, electro-photographic inks, sheetfed inks, overprint varnishes or primers. As already mentioned above, the liquid photoinitiator mixtures are suitable also for producing printing plates e.g. flexo printing plates or offset printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Printing inks are known to the person skilled in the art, are used widely in the art and are described in the literature.

They are, for example, pigmented printing inks and printing inks coloured with dyes. A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 15% by weight, based on the total weight of the printing ink.

The printing inks can be used, for example, for intaglio printing, gravure printing, flexographic printing, screen printing, offset printing, lithography or continuous or dropwise ink-jet printing on material pretreated in accordance with the process of the invention using generally known formulations, for example in publishing, packaging or shipping, in logistics, in advertising, in security printing or in the field of office equipment.

Suitable printing inks are both solvent-based printing inks and water-based printing inks.

Of interest are, for example, printing inks based on aqueous acrylate. Such inks are to be understood as including polymers or copolymers that are obtained by polymerisation of at least one monomer containing a group

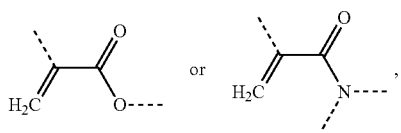

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry oxidatively. The printing inks are dried in a known manner customary in the art, optionally with heating of the coating.

A suitable aqueous printing ink composition comprises, for example, a pigment or a combination of pigments, a dispersant and a binder.

Subject of the invention therefore also is a photopolymerizable composition as described above as further additive (D) comprising a dispersant or a mixture of dispersants.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids. Such dispersants are known and are described, for example, in U.S. Pat. No. 5,186,846 and DE19727767. Suitable oxalkylated phenols are likewise known and are described, for example, in U.S. Pat. No.4,218,218 and DE19727767. Suitable non-ionic dispersants are, for example, alkylene oxide adducts, polymerisation products of vinylpyrrolidone, vinyl acetate or vinyl alcohol and co- or terpolymers of vinyl pyrrolidone with vinyl acetate and/or vinyl alcohol.

It is also possible, for example, to use polymeric acids which act both as dispersants and as binders.

Examples of suitable binder components that may be mentioned include (meth)-acrylate-group-containing, vinyl-group-containing and/or, depending on the intended application, epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP704469, EP012339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally 1% by weight, based on the weight of the preparation.

Printing inks include, for example, those comprising a dye (with a total content of dyes of e.g. from 1 to 35% by weight, based on the total weight of the ink). Dyes suitable for colouring such printing inks are known to the person skilled in the art and are widely available commercially, e.g. from BASF SE.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_6$alkylene glycols and thioglycols, further polyols, e.g. glycerol and C1-C4alkyl ethers of polyhydric alcohols, usually in an amount of from 2 to 30% by weight, based on the total weight of the printing ink.

The printing inks may also, for example, comprise solubilisers, e.g. ε-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed. Suitable substrates are, for example, textile fibre materials, paper, plastics or aluminium foils pretreated by the process according to the invention. Suitable recording systems are e.g. commercially available ink-jet printers.

Preference is given to printing processes in which aqueous printing inks are used. Preferred in ink-jet ink formulations comprise (meth)acrylated epoxy esters; (meth)-acrylated polyesters or vinyl-ether-group-containing polyesters, (meth)acrylated polyurethanes, polyethers and polyols.

A preferred component used in UV-curable inkjet are acrylates which have been modified by reaction with primary or secondary amines, as described, for example, in U.S. Pat. No. 3,844,916, EP280222, U.S. Pat. Nos. 5,482,649 or 5,734,002. Such amine-modified acrylates are also termed aminoacrylates. Examples are already given hereinbefore. It is known that in the presence of aminoacrylates UV-curable systems show an increased curing performance. They are useful to overcome the oxygen inhibition typically observed for radical induced polymerization reactions, especially for low viscous systems like UV-curable inkjet.

It will be clear that mixtures of all these cited monomers, prepolymers, polymers and oligomers can be used in the ink compositions comprising the liquid photoinitiator mixture according to the present invention.

The amount of the photopolymerizable monomer, oligomer or prepolymer in this connection is for example 10 to 80wt %, preferably 10 to 60wt %.

The inks comprising the photoinitiator of the present invention may besides to radically polymerizable components also comprise cationic-curable compositions having a low viscosity which comprise at least one aliphatic or aromatic epoxide, at least one polyol or polyvinyl polyols as mentioned above, and at least one cation-generating photoinitiator. A number of these epoxides are well known in the art and are commercially available. Photoinitiators that can be used in the cationic photocurable compositions are, for example, aryl iodonium salts and aryl sulfonium salts.

Emphasized are such hybrid systems that contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins. Examples are also as given above. Furthermore interesting are hybrid systems that are photopolymerized in a first stage and then crosslinked through thermal post-treatment in a second stage or vice versa. Such hybrid systems comprise an unsaturated compound in admixture with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins. Other compositions suitable as for example ink-jet inks are dual cure compositions, which are cured first by heat and subsequently by UV or electron irradiation, or vice versa, and whose components contain ethylenic double bonds as described above capable to react on irradiation with UV light in presence of a photoinitiator, in the context of the invention the liquid photoinitiator mixture as described above. Ink jet inks for example contain a colorant. A wide variety of organic and inorganic dyes and pigments, alone or in combination may be selected for use in ink jet ink compositions; the person skilled in the art is familiar with the appropriate choice. The pigment particles should be sufficiently small (0.005 to 15 µm) to permit free flow of the ink at the ejecting nozzles. The pigment particles should preferably be 0.005 to 1 µm. Very fine dispersions of pigments and their preparation are disclosed in e.g. U.S. Pat. No. 5,538,548.

The inks preferably comprise a total content of colorant of 1 to 35% by weight, in particular 1 to 30% by weight, and preferably 1 to 20% by weight, based on the total weight of ink. A limit of 2.5% by weight, in particular 5% by weight, and preferably 7.5% by weight, is preferred here as the lower limit.

Suitable colorants are for example pure pigment powders such as Cyan IRGALITE® Blue GLO (BASF SE) or pigment preparations such as MICROLITH-pigment preparations.

Ink jet inks may include a variety of further additives such as for example surfactants, biocides, buffering agents, antimould agents, pH adjustment agents, electric conductivity adjustment agents, chelating agents, anti-rusting agents, polymerisation inhibitors, light stabilizers, and the like. Such additives may be included in the ink jet inks in any effective amount, as desired.

A preferred field of use comprises overprint coatings and also pigmented thin coatings (layer thickness <20 µm), for example printing inks that are used in printing methods such as, for example, flexographic printing, offset printing, screen printing, intaglio printing, gravure printing, letterpress printing, tampon printing and inkjet printing. Overprint coatings typically comprise ethylenically unsaturated compounds such as oligomeric and/or monomeric acrylates. Amine acrylates may also be included.

As mentioned hereinbefore, the overprint coatings and printing inks may also comprise further photoinitiators and coinitiators.

Subject of the invention therefore also is a photopolymerizable composition as described above, which is a printing ink, in particular an offset printing ink.

The liquid photoinitiator mixtures of the present invention are also suitable for use in UV-curable adhesives; e.g. in the preparation of pressure-sensitive adhesives, laminating adhesives, hot-melt adhesives, moisture-cure adhesives, silane reactive adhesives or silane reactive sealants and the like, and related applications. Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

The liquid photoinitiator mixtures according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

The liquid photoinitiator mixtures according to the invention may also be used as free-radical photoinitiators or photoinitiating systems for radiation-curable powder coatings. The powder coatings may be based on solid resins and monomers containing reactive double bonds, for example maleates, fumarates, vinyl ethers, (meth)acrylates, (meth)acrylamides and mixtures thereof. A free-radical UV-curable powder coating may be formulated by mixing unsaturated polyester resins with solid acrylamides (e.g. methylacrylamido-glycolate methyl ester) and a free-radical photoinitiator according to the invention, for example as described in the lecture "Radiation Curing of Powder Coating", Conference Proceedings, Radtech Europe 1993 by M. Wittig and Th. Gohmann. Free-radical UV-curable power coatings may also be formulated by mixing unsaturated polyester resins with solid acrylates, methacrylates or vinyl ethers and a photoinitiator (or photoinitiator mixture) according to the invention. The powder coatings may also comprise binders, as described in, for example, DE4228514 and EP636669. The powder coating formulations described in EP636669 comprise, for example, a) an unsaturated resin from the group of (semi-)crystalline or amorphous unsaturated polyesters, unsaturated polyacrylates or mixtures thereof with unsaturated polyesters, with special preference being given to those derived from maleic acid or fumaric acid; b) an oligomeric or polymeric crosslinking agent containing vinyl ether-, vinyl ester- or (meth)acrylate-functional groups, with special preference being given to vinyl ether oligomers, for example divinyl ether-functionalised urethanes; c) the photoinitiator.

The UV-curable powder coatings may also comprise white or coloured pigments. Accordingly, for example, there may preferably be used rutile titanium dioxide in concentrations of up to 50% by weight in order to obtain a cured powder coating with good hiding power. The process normally comprises electrostatic or tribostatic spraying of the powder onto the substrate, e.g. metal or wood, melting of the powder as a result of heating and, after a smooth film has been formed, radiation-curing of the coating using ultraviolet and/or visible light, for example using medium-pressure mercury lamps, metal halide lamps or xenon lamps. A particular advantage of radiation-curable powder coatings compared to corresponding thermally curable coatings is that the flow time after melting of the powder particles can be extended as desired in order to ensure the formation of a smooth high-gloss coating. In contrast to thermally curable systems, radiation-curable powder coatings can be formulated so that they melt at relatively low temperatures, without the undesirable effect of a reduction in shelf-life. For that reason they are also suitable as coatings for heat-sensitive substrates, for example wood or plastics. However, if the powder coatings are to be applied to non-heat-sensitive substrates, for example metals (vehicle coatings), it is also possible to make available "dual cure" powder coating formulations using the photoinitiators according to the invention. Such formulations will be known to the person skilled in the art; they are cured both thermally and also by means of UV and can be found in, for example, U.S. Pat. No. 5,922,473.

The liquid photoinitiator mixtures according to the invention may also be used in the form of an aqueous, for example 0.5-5%, preferably 0.5-2%, dispersion in polymer dispersions, for example in aqueous polyurethane dispersions, so-called PUDs.

The photocurable compositions according to the invention are suitable, for example, as coating substances for substrates of all kinds, e.g. wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which a protective layer or, by means of image-wise exposure, an image is to be applied.

The substrates can be coated by applying a liquid composition, a solution or a suspension or a powder to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents are, for example, ketones, ethers and esters, e.g. methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by printing methods such as flexography printing, lithography printing, inkjet, screen printing, spin-coating, immersion, roller application, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Ed., Vol. A18, pp. 491-500.

The amount applied (layer thickness) and the nature of the substrate (layer support) are dependent on the desired field of use.

A further field of use comprises compositions that are suitable for the coating of glass fibres, both for the inner and also for the middle and outer layers. The coated glass fibres may also be gathered into bundles giving a further coating. Such coating layers comprise UV-curable oligomers, UV-curable monomers and also at least one photoinitiator and additives.

Any UV-curable oligomer is suitable for the coating of glass fibres.

Further fields of use of photocuring are metal coating, for example the application of a finish to sheet metals and tubes, cans or bottle closures, and also photocuring on plastics coatings, for example PVC-based floor or wall coverings.

Examples of the photocuring of paper coatings are the application of a colourless finish to labels, packaging materials or book covers.

The liquid photoinitiator mixtures according to the invention, or blends of the liquid photoinitiator mixtures according to the invention with other photoinitiators, may also be used as free-radical photoinitiators or photoinitiating systems in formulations used for rapid prototyping or additive manufacturing processes based on photolithographic techniques.

Such processes are well-known to the one skilled in the art and include for example stereolithography using a moving laser (SLA process), digital light processing (DLP) or large area maskless photopolymerization (LAMP). Common to all these techniques is the stepwise build-up of three-dimensional objects by a layer-by-layer image-wise curing process using one of the aforementioned techniques, followed by the removal of uncured material by a suitable washing or development process. The image-wise curing process can be combined with a full-exposure irradiation step, or with a thermal curing process, in order to achieve the desired final properties. The aforementioned post curing processes are subsequently applied, preferably minutes to few hours after completion of the preceding layer wise form giving process. In the irradiation step various light sources, e.g. mercury lamps, xenon and fluorescent lamps or light emitting diodes (LEDs) may be used.

It is also possible to combine the radically curing material with a second material curing by an alternative mechanism. An example is the combination of the radically curing formulation with a cationically curing material. For example, acrylate moieties contained in a formulation are preferably polymerized using radical initiators, whereas the polymerization of epoxy moieties is preferably triggered by cationic initiators. Both processes can be applied simultaneously or can be combined in a subsequent manner.

Alternatively rapid prototyping or additive manufacturing can also be performed using 3D printing respectively polyjetting technologies. Corresponding equipment is commercially available from e.g. 3D Systems Inc. under their ProJet™ brand or from Stratasys offering their PolyJet 3D printers under their brands Dimension, Connex, Eden and Pro. These examples are intended for reference only, but should not limit the scope of the invention to related 3D printing technologies. In these technologies the three-dimensional objects are build-up by layer-by-layer jetting of the photocurable material, followed by immediate curing using a suitable radiation source. Suitable radiation sources are for example irradiation systems commonly used in radiation curing, such as mercury lamps, doped mercury lamps, electrodeless lamps and the like, or LED lamps of suitable wavelengths.

In these rapid prototyping or additive manufacturing applications, the liquid photoinitiator mixtures according to the invention can be used in the photopolymer material used for the production of the three-dimensional object, or in the support material used as an intermediate support for the build-up of three-dimensional structures. The support material is designed in a way that it can easily be removed after the build-up of the three-dimensional object without affecting the latter, e.g. by a suitable washing or development process.

The liquid photoinitiator mixtures according to the invention, or blends of the liquid photoinitiator mixtures according to the invention with other photoinitiators, may also be used as free-radical photoinitiators or photoinitiating systems in formulations used for applications using LED (light-emitting diode) light sources for curing. LED lights sources find for example use for the curing of UV inkjet inks, for example in high-speed single pass applications, sheetfed applications, narrow web applications, flat bed application, or wide format applications. Especially designed LED curable inks are also used in prototyping or additive manufacturing processes using the photopolymer jetting technology. LED light sources are also used in industrial applications, such as e.g. wood coatings. Other applications using LED light sources are field applications, such as repair applications, e.g. automotive or industrial repair coatings, or construction side applications such as flooring applications. Other applications are adhesives both for professional and do-it-yourself applications. Still other applications are found in light curable nail polishes and the like.

LED light sources emitting at different wavelengths extending form the visible to the short UV are available. However in view of the price/performance level of the different LED diodes and process safety considerations, LED emitting in the visible or UV-A are preferred. LED light sources emitting in the visible, for example at 470 nm, are especially preferred for dental or medical applications. LED light sources emitting in the visible or UV-A range, for example at 405 nm, 395 nm, 385 nm or 365 nm are preferred for technical applications. Especially preferred are LEDs emitting at 405 nm, 395 nm or 385 nm. Since the liquid photoinitiator mixtures according to the invention have good absorption in this range and undergo a photobleaching process, they are especially suited for use in such applications.

When using LED light sources for curing, it can be advantageous to use the liquid photoinitiator mixtures according to the invention in combination with another photoinitiator compound (C). Preferred is the combination with (substituted) benzophenone derivatives, phenyl glyoxylate derivatives or thioxanthone derivatives. Especially preferred is the combination of liquid photoinitiator mixtures according to the invention with thioxanthone derivatives.

The photosensitivity of the compositions according to the invention usually extends from approximately 150 nm into the IR range. Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED, OLED), electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible and infrared or NIR range may also be used.

As already mentioned, curing according to the invention can be carried out solely by irradiation with electromagnetic radiation. Depending on the composition of the formulation to be cured, however, thermal curing before, during or after the irradiation is advantageous. Thermal curing is carried out by methods known to the person skilled in the art. In general, the curing is carried out in an oven, e.g. a circulating air oven, on a heating plate or by irradiation with IR lamps. Unassisted curing at room temperature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The invention relates to the use of the liquid photoinitiator mixtures as described above as photoinitiators for the photopolymerization of compositions comprising monomeric or oligomeric compounds containing ethylenically unsaturated double bonds and to a process for the photopolymerization of monomeric, oligomeric or polymeric compounds containing at least one ethylenically unsaturated double bond, which comprises adding to the abovementioned compounds a liquid photoinitiator mixture as described above and irradiating the resulting composition with electromagnetic radiation.

Interesting is the use of the composition as described above for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (H DS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board; in particular the use of a photo-polymerizable composition as described above for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

Subject of the invention is a process as described above for producing coatings, printing inks, printing plates, adhesives, dental compositions, gel coats, photoresists for electronics, for encapsulating electrical and electronic components, for producing magnetic recording materials, for producing micromechanical parts, waveguides, optical switches, plating masks, etch masks, colour proofing systems, glass fibre cable coatings, screen printing stencils, for producing three-dimensional objects by a rapid proto-typing or additive manufacturing technology based on a photolithographic or polymer jetting process using light curable materials (for use as models or prototypes as well as fully functional parts for direct use with excellent mechanical stability and esthetical appearance), for producing image recording material, for holographic recording, for producing microelectronic circuits or for producing decolorizing materials.

Preferred is a process as described above for the production of pigmented and non-pigmented surface coatings, overprint coatings, powder coatings, printing inks, inkjet inks, gel coats, composite materials or glass fibre coatings.

The invention relates also to a coated substrate which is coated on at least one surface with a composition as described above and irradiated with electromagnetic radiation, as well as a polymerized or crosslinked composition obtained by curing a polymerizable composition as described above.

In particular of interest is the use of a composition as described above as a surface coating for food packaging materials, as well as a process as described above for the production of a surface coating for food packaging materials employing a composition as described above.

The liquid photoinitiator mixture according to the present invention can be incorporated into a photocurable formulation in an easy way even at room temperature without raising the temperature and in any wanted ratio. Further, as already stated above, the preparation of photointiator blends comprising besides the liquid bisacylphosphine oxide component for example a liquid hydroxy ketone compound, such as 2-hydroxy-2-methyl-1-phenyl-propanone (Darocur® 1173) or methyl a-oxo benzeneacetate (Darocur® MBF) is easy to perform. The more, also blends with solid photoinitiators, for example a solid hydroxy ketone compound such as 2-hydroxy-1-{4-[4-(2-hydroxy-2-methyl-propionyl)-benzyl]-phenyl}-2-methyl-propan-1-one (Irgacure®127) or with Esacure® KIP (provided by Lamberti SA) can easily be produced. (The Darocur® and Irgacure® products are provided by BASF SE)

In contrast to the known bisacylphosphine compounds, the liquid photoinitiator mixture of the present invention furthermore can be employed in aqueous formulations even without using a dispersant or emulsifier.

Another property of the liquid photoinitiator mixture according to the present invention is the low colouring of the cured formulation directly after the cure.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

EXAMPLES

General: The experiments are performed in a round flask with a magnetic stirrer, distillation equipment and vacuum connection. Solvents are used as received. Analysis is performed using $^1$H- and $^{31}$P-NMR spectroscopy and HPLC (Agilent Zorbax XDB Phenyl, 2.1×150 mm/5 μm reversed phase column at 50° C. The eluent gradient is water (75%)/methanol (25%) to 100% methanol over 20 min, followed by 5 min elution using methanol).

Example 1

Preparation of a Liquid Bisacylphosphine Oxide Mixture Using a Large Excess of Alcohol Under Light Vacuum 3 g (7.2 mmol) [Bis-(2,4,6-trimethyl-benzoyl)-phosphanyl]-acetic acid methyl ester prepared as described in WO06/056541, 40 mg dibutyltin dilaurat and 9.4 g (72 mmol) mixture of octyl alcohols, Exxal 8 (ExxonMobile) are placed in the reaction flask, forming a suspension of the bisacylphosphine oxide in the alcohol. A slight vacuum (280 mbar) is applied and the reaction mixture is heated to 130° C. while stirring. The mixture becomes a clear yellowish solution. The reaction mixture is kept at this temperature for 4 hours while methanol and small amounts of Exxal 8 are distilled off. The progress of the reaction is monitored in regular intervals by HPLC. After 4 hours the ratio methyl ester/octyl ester is >98%. The reaction mixture is cooled to room temperature and the excess alcohol distilled off in high vacuum. An easily pourable yellowish liquid is obtained, which according to $^1$H-NMR-analysis and HPLC analysis consists of 0.2% bis-(2,4,6-trimethyl-benzoyl)-phosphanyl]-acetic acid methyl ester, 92.4% of the mixture of the corresponding octyl esters (of Exxal 8) and 7.4% Exxal 8. The viscosity of the liquid is 3100 mPas at 23° C.

Example 2

Preparation of a Liquid Bisacylphosphine Oxide Mixture Using a Large Excess of Alcohol Under Higher Vacuum The reaction as reported in example 1 is repeated except that a vacuum of 100 mbar is applied. Under these conditions, a ratio methyl ester/octyl ester of 96:4 is reached after only one hour at 130° C. After isolation a yellowish liquid containing 88% of the mixture of octyl esters of bis-(2,4,6-trimethyl-benzoyl)-phosphanyl]-acetic acid, 4% bis-(2,4,6-trimethyl-benzoyl)-phosphanyl]-acetic acid methyl ester and 8% Exxal 8 is obtained.

Example 3

Preparation of a Liquid Bisacylphosphine Oxide Mixture Using a Large Excess of Alcohol Under Higher Vacuum and Zr(acac)$_4$ as Catalyst The reaction as reported in example 2 is repeated except that zirconium(IV)acetyl acetate is used as catalyst instead of dibutyltin dilaurat. Under these conditions, a ratio methyl ester/octyl ester of 96:4 is reached after 4 hours at 130° C. After isolation a yellowish liquid containing 89% of the mixture of octyl esters of bis-(2,4,6-trimethyl-benzoyl)-phosphanyl]-acetic acid, 4% bis-(2,4,6-trimethyl-benzoyl)-phosphanyl]-acetic acid methyl ester and 7% Exxal 8 is obtained.

Example 4

Preparation of a Liquid Bisacylphosphine Oxide Mixture Using a Small Excess of Alcohol Under Higher Vacuum and Zr(acac)$_4$ as Catalyst 3 g (7.2 mmol) [Bis-(2,4,6-trimethyl-benzoyl)-phosphanyl]-acetic acid methyl ester prepared as described in WO06/056541, 40 mg zirconium(IV)acetyl acetate and 1.4 g (8 mmol) Exxal 8 (ExxonMobile) are placed in the reaction flask. A light vacuum of 100 mbar is applied and the reaction mixture slowly heated to 130° C. The reaction mixture is kept at 130° C. while methanol and small amounts of Exxal 8 are distilled off. The progress of the reaction is monitored in regular intervals by HPLC. After 6.5 hours the ratio methyl ester/octyl ester is 92:8. The reaction mixture is cooled to room temperature. An easily pourable yellowish liquid is obtained without distillation of excess alcohol, which according to $^1$H-NMR-analysis and HPLC analysis consist of 8% bis-(2,4,6-trimethyl-benzoyl)-phosphanyl]-acetic acid methyl ester, 88% of the mixture of esters corresponding to the Exxal 8 and 4% Exxal 8.

Example 5

Preparation of a Liquid Bisacylphosphine Oxide Mixture Using a Small Excess of Alcohol Under Higher Vacuum and Cyclohexane as Entrainer 3 g (7.2 mmol) [Bis-(2,4,6-trimethyl-benzoyl)-phosphanyl]-acetic acid methyl ester prepared as described in WO06/056541, 40 mg zirconium(IV)acetyl acetate, 1.4 g (8 mmol) Exxal 8 (ExxonMobile) and 50 ml cyclohexane are placed in the reaction flask forming a turbid suspension. The reaction mixture is slowly heated to 100° C. while stirring without applying vacuum. The reaction mixture becomes a clear yellowish solution. Cyclohexane containing methanol is continuously distilled off and replaced by approximately the same amount of fresh cyclohexane. After 6 hours the ratio methyl ester/octyl ester is 94:6. The reaction mixture is cooled to room temperature. Cyclohexane is distilled off in vacuum providing an easily pourable yellowish liquid, which according to $^1$H-NMR-analysis and HPLC analysis consist of 5% bis-(2,4,6-trimethyl-benzoyl)-phosphanyl]-acetic acid methyl ester, 92% of the mixture of the esters corresponding to Exxal 8 and 3% Exxal 8.

Example 6

Preparation of a Liquid Bisacylphosphine Oxide Mixture Using a Small Excess of a Mixture of Isomeric Nonanols Under Higher Vacuum and Zr(acac)$_4$ as Catalyst 622 g (1.5 mol) [bis(2,4,6-trimethylbenzoyl)phosphanyl] acetic acid methyl ester prepared as described in WO06/056541 is added in 5 portions to 238 g (1.65 mol) Nonanol N at 70° C. over 30 min. 1.8 g (0.00375 mol) of zirconium (IV) acetylacetonate is then added and the reaction mixture heated to 95° C. and placed under a vacuum of 60 mbar. Four additional 1.8 g portions zirconium(IV) acetylacetonate are added over the next 4 hours and, subsequently, the reaction mixture is held at 95° C. for a further 2 h. During the course of the reaction, methanol and a small amount of Nonanol N are removed by distillation. At the end of the reaction, a yellow oil is obtained which consists of 87% of isomeric [bis(2,4,6-trimethylbenzoyl)phosphanyl]acetic acid nonyl esters, 8.5% [bis(2,4,6-trimethyl-benzoyl)phosphanyl]acetic acid methyl ester and 4.5% Nonanol N by HPLC analysis.

Example 7

Preparation of a Liquid Bisacylphosphine Oxide Mixture Using 1,6-hexandiol in Toluene and 1,5,7-triazabicyclo[4.4.0]dec-5-ene as Catalyst 3.03 g (7.3 mmol) [bis(2,4,6-trimethylbenzoyl)phosphanyl]acetic acid methyl ester prepared as described in WO06/

056541 and 0.44 g 1,6-hexandiol (3.7 mmol) are suspended in 40 ml toluene. 0.05 g 1,5,7-triazabicyclo[4.4.0]dec-5-ene are added and the mixture is heated to 130° C. Toluene is distilled off during the reaction and continuously replaced by the same amount of solvent. After 8 hours the mixture is cooled to room temperature and volatiles are removed in vacuum. 3.25 g of a yellowish oil is obtained which consists according to NMR analysis of 1,6-hexandiol [bis(2,4,6-trimethyl-benzoyl)phosphanyl]acetic acid diester (approximately 55%), 1,6-hexandiol [bis(2,4,6-trimethylbenzoyl)phosphanyl]acetic acid monoester (31%), bis(2,4,6-trimethyl-benzoyl)-phosphanyl]acetic acid methyl ester (8%) and 1,6-hexandiol (6%).

Example 8

Preparation of a Liquid Bisacylphosphine Oxide Mixture Using 1,4-bis(hydroxymethyl)cyclohexane in Cyclohexne and 1,5,7-triazabicycle-[4.4.0]dec-5-ene as Catalyst 8.29 g (20 mmol) [bis(2,4,6-trimethylbenzoyl)phosphanyl]acetic acid methyl ester prepared as described in WO06/056541 and 0.72 g 1,4-bis(hydroxymethyl)cyclohexane (5 mmol) are suspended in 50 ml cyclohexane. 0.001 g 1,5,7-triazabicyclo[4.4.0]dec-5-ene are added and the mixture is heated to 80° C. Cyclohexane is distilled off during the reaction and continuously replaced by the same amount of solvent. After 9 hours the mixture is cooled to room temperature and volatiles are removed in vacuum. 3.25 g of a yellowish viscous oil is obtained which consists according to NMR analysis of 1,4-bis(hydroxymethyl)cyclohexane [bis(2,4,6-trimethylbenzoyl)phosphanyl]acetic acid di-ester (approximately 65%), 1,4-bis(hydroxymethyl)cyclohexane [bis(2,4,6-trimethyl-benzoyl)phosphanyl]acetic acid monoester (27%), and bis(2,4,6-tri methyl-benzoyl)-phosphanyl]acetic acid methyl ester (8%).

Application Examples

Example A1

Storage Stability 3 g of the liquid bisacylphosphine oxide photoinitiator obtained according to example 4 are placed under air in a brown flask. The flask is closed by a stopper and stored under exclusion of light using a "heat and freeze" cycle during which the storage temperature is altered in regular intervals (1 day) between room temperature (22-24° C.) and freezer temperature (3° C.). The condition of the liquid is visually evaluated once per week. After 6 months of storage under these conditions, the photoinitiator is still liquid without any formation of solid parts and easily pourable at room temperature.

Example A2

Dissolution in Monomers

The time and conditions for completely dissolving 2% of bisacylphosphine oxide photoinitiators in different monomers is evaluated.

2% of the bisacylphosphine oxide photoinitiator and 98% of the monomer are placed in a beaker equipped with a magnetic stirring bar and a heating bath. The mixture is visually evaluated and the time and conditions when a clear solution is formed is rated.

| rating | dissolved after |
|---|---|
| 1 | 15 min at room temperature |
| 2 | 10 min at 40° C. |
| 3 | 10 min at 50° C. |
| 4 | 10 min at 60° C. |
| 5 | >10 min at 60 C. |

The following results are obtained (average of 5 measurements):

| Photoinitiator | HDDA | TPGDA | TMPTA |
|---|---|---|---|
| bis(2,4,6-trimethylbenzoyl)-phenyl phosphine oxide (Irgacure ® 819) | 2.5 | 3.8 | 4.7 |
| bis(2,4,6-trimethyl-benzoyl)-phosphanyl]-acetic acid methyl ester | 2.1 | 2.2 | 2.8 |
| bisacylphosphine oxide photoinitiator obtained according to example 4 | 1 | 1 | 1 |

HDDA = 1,6-hexanediol diacrylate
TPGDA = tripropylene glycol diacrylate
TMPTA = trimethylolpropane triacrylate Example A3

Photoinitiator Performance in a White Pigmented Polyester Acrylate Coating

Photocurable white-pigmented polyester acrylate formulations are prepared, comprising 2% of the photoinitiator to be tested. The formulations are applied onto white-coated chipboards in a thickness of 100 □m and cured with a 80 W mercury medium pressure lamp by passing the samples on a belt under the lamp with a belt speed of 5 m/min.

Determined are curing performance via the pendulum hardness (PH) in seconds according to Konig DIN 53157. The higher the PH value, the more reactive is the tested photoinitiator compound. The yellowing of the formulation after curing is determined via colorimetric determination of the b* value according to the Cielab system. The higher the value, the more colored is the cured coating.

The following results are obtained:

| Photoinitiator | PH [s] | b* |
|---|---|---|
| bis(2,4,6-trimethylbenzoyl)-phenyl phosphine oxide (Irgacure ® 819) | 161 | 4.2 |
| bis(2,4,6-trimethyl-benzoyl)-phosphanyl]-acetic acid methyl ester | 161 | 4.1 |
| bisacylphosphine oxide photoinitiator obtained according to example 4 | 161 | 3.3 |

Example A4

Photoinitiator Performance in Different White Pigmented Photocurable Formulations Using Phenyl-1-hydroxycyclohexyl Ketone as Additional Photoinitiator (C)

The following photocurable formulations are prepared:

Formulation 1

40.0% by wt of a polyester acrylate (Laromer® PE9074, provided by BASF SE)
34.3% by wt of dipropylene glycol diacrylate (Laromer® DPGDA, provided by BASF SE)
0.2% by wt of a slip aid (EFKA® 3030, provided by BASF SE)
0.5% by wt of a wetting aid (EFKA® 5220, provided by BASF SE)
21.0% by wt of titanium dioxide (Kronos® 2300, provided by Kronos)
1.0% by wt of the photoinitiator according to example 6
3.0% by wt of phenyl-1-hydroxycyclohexyl ketone (Irgacure® 184, provided by BASF SE)

Formulation 2

30.0% by wt of a polymer based on: polyetherpolyol; epoxy resin; acrylic ester (Laromer® LR8986, provided by BASF SE
22.3% by wt of an amine modified polyetheracrylate (PO77F, provided by BASF)
22.0% by wt of tripropylene glycol diacrylate (TPGDA)
0.2% by wt of a slip aid (EFKA® 3030, provided by BASF SE)
0.5% by wt of a wetting aid (EFKA® 5220, provided by BASF SE)
21.0% by wt of titanium dioxide
1.0% by wt of the photoinitiator according to example 6
3.0% by wt of phenyl-1-hydroxycyclohexyl ketone (Irgacure® 184, provided by BASF SE)

Formulation 3

58.3% by wt of an amine modified polyetheracrylate (PO94F provided by BASF)
16.0% by wt of a polyester acrylate (Laromer® PE9079, provided by BASF SE)
0.2% by wt of a slip aid (EFKA® 3030, provided by BASF SE)
0.5% by wt of a wetting aid (EFKA® 5220, provided by BASF SE)
21.0% by wt of titanium dioxide
1.0% by wt of the photoinitiator according to example 6
3.0% by wt of phenyl-1-hydroxycyclohexyl ketone (Irgacure® 184, provided by BASF SE)

Formulation 4

30.0% by wt of a polymer based on: polyetherpolyol; epoxy resin; acrylic ester (Laromer® LR8986, provided by BASF SE
22.3% by wt of an amine modified polyetheracrylate (PO77F, provided by VSF)
22.0% by wt of tripropylene glycol diacrylate (TPGDA)
0.2% by wt of a slip aid (EFKA® 3030, provided by BASF SE)
0.5% by wt of a wetting aid (EFKA® 5220, provided by BASF SE)
21.0% by wt of titanium dioxide
2.0% by wt of the photoinitiator according to example 6
2.0% by wt of phenyl-1-hydroxycyclohexyl ketone (Irgacure® 184, provided by BASF SE)

A4.1: Reactivity

The formulation to be tested is applied with a bar coater on white coil with a thickness of 24 μm. Curing of the formulation is achieved by moving the sample on a belt under a UV Hg high pressure lamp (200 W/cm) with a defined speed. The highest speed which can be used to fully cure the formulation is determined (Full cure is determined by finger nail scratching). The results are collected in the following table 1.

A4.2: Yellowing

The formulation to be tested is applied on white coil with a thickness of 100 μm. Curing of the formulation is achieved by moving the sample on a belt under a Hg lamp (200 W/cm) at a belt speed of 5 m/min. The yellowing of the formulation is determined directly after curing, after 1 h, after 72 h and after further irradiation with a TL03 lamp, via colorimetric determination of the b* value according to the Cielab system. The higher the value, the more yellowish is the cured coating. The results are collected in the following table 1.

A4.3: Pendulum Hardness

The formulation to be tested is applied on white coil with a thickness of 100 μm. Curing of the formulation is achieved by moving the sample on a belt under a Hg lamp (200 W/cm) at a belt speed of 5 m/min. The pendulum hardness (PH) in seconds according to Konig DIN 53157 is determined directly after curing and 72h after storing in a temperature-controlled room at 22° C. The higher the PH value, the more reactive is the tested photoinitiator compound. The results are collected in the following table 1.

A4.4: Maximum Curable Film Thickness

The formulations are poured into a lid of a polyethylene cup, so that the wet thickness is about 2 mm and cured with a 200 W gallium-doped mercury medium pressure lamp by passing the samples on a belt under the lamp with a belt speed of 5 m/min. Then the cured layer is removed from the lid and any uncured material is removed with acetone, dried and the thickness of the sample is measured.

Determined is the maximum film thickness curable under these conditions. The results are collected in the following table 1.

TABLE 1

| Example | Formulation 1 | Formulation 2 | Formulation 3 | Formulation 4 |
|---|---|---|---|---|
| A4.1; reactivity: | | | | |
| belt speed [m/min] | 20 | 30 | 70 | 45 |
| A4.2: yellowing | | | | |
| b* directly after curing | 2.2 | 2.2 | 2.3 | 3.2 |
| b* after 1 h | 2.1 | 1.7 | 2.2 | 2.7 |
| b* after 72 h | 1.9 | 1.6 | 2.2 | 2.6 |
| b* after further irradiation | 0.3 | −0.3 | 0.3 | −0.2 |
| A4.3: pendulum hardness [s] | | | | |
| directly after curing | 63 | 81 | 34 | 88 |
| after 72 h | 73 | 80 | 21 | 87 |
| A4.4: maximum film thickness cured [μm] | 206 | 281 | 253 | 223 |

Example A5

Photoinitiator Performance in a Photocurable Blue Coating Formulation Using Phenyl-1-hydroxycyclohexyl Ketone as Additional Photoinitiator (C)

The Following Photocurable Formulations 5a-5c are Prepared:

Basic Blue Coating Formulation:

| | |
|---|---|
| 20.0 g | of trimethylolpropane triacrylate (TMPTA) |
| 40.0 g | of an amine modified polyetheracrylate (PO94F provided by BASF) |
| 30.0 g | of a polyester acrylate (Laromer® PE9079, provided by BASF SE) |
| 0.2 g | of a slip aid (EFKA® 3030, provided by BASF SE) |
| 0.8 g | of a wetting aid (EFKA® 7731, provided by BASF SE) |
| 5.0 g | of Heliogen Blue 7110F (PB15:4 blue pigment, by BASF SE) |
| 3.0 g | of phenyl-1-hydroxycyclohexyl ketone (Irgacure®184, provided by BASF SE) |

To the Basic Formulation the Following Amounts of Photoinitiator are Added:

Formulation 5a: 0.5 g of the photoinitiator according to example 6

Formulation 5b: 1.0 g of the photoinitiator according to example 6

Formulation 5c: 1.5 g of the photoinitiator according to example 6

A5.1: Reactivity

The formulation to be tested is applied on white coil with a thickness of 25 µm. Curing of the formulation is achieved by moving the sample on a belt under a Hg lamp (120 W/cm) followed by a Ga-doped Hg lamp (120 W/cm) with a defined speed. The highest speed which can be used to fully cure the formulation (finger nail test) is determined. The results are collected in the following table 2.

A5.2: Maximum Curable Film Thickness

The formulations are poured into a lid of a polyethylene cup, so that the wet thickness is about 2 mm and cured with a 200 W gallium-doped mercury medium pressure lamp by passing the samples on a belt under the lamp with a belt speed of 5 m/min. Then the cured layer is removed from the lid and any uncured material is removed with acetone, dried and the thickness of the sample is measured.

Determined is the maximum film thickness curable under these conditions. The results are collected in the following table 2.

TABLE 2

| Example | Formulation 5a | Formulation 5b | Formulation 5c |
|---|---|---|---|
| A5.1; reactivity by belt speed [m/min] | 50 | 70 | 90 |
| A5.2: maximum film thickness cured [µm] | 175 | 220 | 215 |

Example A6

Photoinitiator Performance in a Photocurable Yellow Coating Formulation Using Phenyl-1-hydroxycyclohexyl Ketone as Additional Photoinitiator (C)

The Following Photocurable Formulations 6a-6c are Prepared:
Basic Yellow Coating Formulation:

| | |
|---|---|
| 20.0 g | of trimethylolpropane triacrylate (TMPTA) |
| 40.0 g | of an amine modified polyetheracrylate (PO94F provided by BASF) |
| 30.0 g | of a polyester acrylate (Laromer® PE9079, provided by BASF SE) |
| 0.2 g | of a slip aid (EFKA® 3030, provided by BASF SE) |
| 0.8 g | of a wetting aid (EFKA® 7731, provided by BASF SE) |
| 5.0 g | of Paliotol Yellow L0962HD (PY 138, yellow pigment, by BASF SE) |
| 3.0 g | of phenyl-1-hydroxycyclohexyl ketone (Irgacure®184, provided by BASF SE) |

To the Basic Formulation the Following Amounts of Photoinitiator are Added:

Formulation 6a: 0.5 g of the photoinitiator according to example 6

Formulation 6b: 1.0 g of the photoinitiator according to example 6

Formulation 6c: 1.5 g of the photoinitiator according to example 6

A6.1: Reactivity

The reactivity evaluation is performed as described for A5.1. The results are collected in the following table 3.

A6.2: Maximum Curable Film Thickness

Evaluation of the maximum curable film thickness is performed as described for A5.21. The results are collected in the following table 3.

TABLE 3

| Example | Formulation 6a | Formulation 6b | Formulation 6c |
|---|---|---|---|
| A6.1; reactivity by belt speed [m/min] | 50 | 50 | 60 |
| A6.2: maximum film thickness cured [µm] | 37 | 45 | 45 |

Example A7

Photoinitiator Performance in a Photocurable Red Coating Formulation Using phenyl-1-hydroxycyclohexyl Ketone as Additional Photoinitiator (C)

The Following Photocurable Formulations 7a-7c are Prepared:
Basic Red Coating Formulation:

| | |
|---|---|
| 20.0 g | of trimethylolpropane triacrylate (TMPTA) |
| 40.0 g | of an amine modified polyetheracrylate (PO94F provided by BASF) |
| 30.0 g | of a polyester acrylate (Laromer® PE9079, provided by BASF SE) |
| 0.2 g | of a slip aid (EFKA® 3030, provided by BASF SE) |
| 0.8 g | of a wetting aid (EFKA® 7731, provided by BASF SE) |
| 5.0 g | of Iragazin® Red L3670HD (PR254, red pigment, provided by BASF) |
| 3.0 g | of phenyl-1-hydroxycyclohexyl ketone (Irgacure® 184, provided by BASF SE) |

To the Basic Formulation the Following Amounts of Photoinitiator are Added:

Formulation 7a: 0.5 g of the photoinitiator according to example 6

Formulation 7b: 1.0 g of the photoinitiator according to example 6

Formulation 7c: 1.5 g of the photoinitiator according to example 6

A7.1: Reactivity

The reactivity evaluation is performed as described for A5.1. The results are collected in the following table 4.

A7.2: Maximum Curable Film Thickness

Evaluation of the maximum curable film thickness is performed as described for A5.21. The results are collected in the following table 4.

TABLE 4

| Example | Formulation 6a | Formulation 6b | Formulation 6c |
| --- | --- | --- | --- |
| A7.1; reactivity by belt speed [m/min] | 45 | 50 | 50 |
| A7.2: maximum film thickness cured [µm] | 45 | 50 | 50 |

Example A8

Curing Performance of the Photoinitiator According to Example 6 Alone and in Combination with phenyl-1-hydroxycyclohexyl Ketone as Additional Photoinitiator (C) in a White Pigmented Photocurable Formulation The Following Photocurable Formulations 8a-8b are Prepared:
Basic White Coating Formulation

| | |
| --- | --- |
| 15.0 g | of trimethylolpropane triacrylate (TMPTA) |
| 35.3 g | of an amine modified polyetheracrylate (PO94F provided by BASF) |
| 20.0 g | of a polyester acrylate (Laromer® PE9079, provided by BASF SE) |
| 0.2 g | of a slip aid (EFKA® 3030, provided by BASF SE) |
| 0.8 g | of a wetting aid (EFKA® 5220, provided by BASF SE) |
| 25.0 g | of titanium dioxide (TiO₂ CL 2310) |

To the Basic Formulation the Following Amounts of Photoinitiator are Added:

Formulation 8a: 1.0 g of the photoinitiator according to example 6 and 3.0 g phenyl-1-hydroxycyclohexyl ketone (Irgacure®184, provided by BASF) as additional photoinitiator (C)

Formulation 8b: 4.0 g of the photoinitiator according to example 6

A8.1: Reactivity

The reactivity evaluation is performed as described for A5.1. The results are collected in the following table 5.

A8.2: Maximum Curable Film Thickness

Evaluation of the maximum curable film thickness is performed as described for A5.2. The results are collected in the following table 5.

A8.3 Storage Stability

In order to check the storage stability of the ready-to-use formulations 8a and 8b, the two formulations are stored at 40° c for 3 months. After this time the evaluation tests A8.1 and A8.2 are repeated. The results are collected in the following table 5.

TABLE 5

| Example | Formulation 8a | Formulation 8b |
| --- | --- | --- |
| A7.1; reactivity by belt speed [m/min] | 70 | 30 |
| after 3 months storage at 40° C. | 70 | 35 |
| A7.2: maximum film thickness cured [µm] | 210 | 175 |
| after 3 months storage at 40° C. | 210 | 165 |

Example A9

Curing Performance of the of the Photoinitiator According to Example 6 in Combination with Different Additional Photoinitiators (C) in a White Pigmented Photocurable Formulation The Following Photocurable Formulations 9a-9e are Prepared:
Basic White Coating Formulation

| | |
| --- | --- |
| 80.3% | by wt of an epoxy acrylate (Laromer® LR898/6, provided by BASF SE) |
| 0.2% | by wt of a slip aid (EFKA® 3030, provided by BASF SE) |
| 0.5% | by wt of a wetting aid (EFKA® 5220, provided by BASF SE) |
| 15.0% | by wt of titanium dioxide (TiO₂ CL 2310) |

To the Basic Formulation the Following Amounts of Photoinitiator are Added:

Formulation 9a: 1.0% by wt of the photoinitiator according to example 6 and 3.0% by wt of a difunctional α-hydroxy ketone (Esacure® ONE, provided by Lamberti Spa) as additional photoinitiator (C)

Formulation 9b: 1.0% by wt of the photoinitiator according to example 6 and 3.0% by wt of 2-hydroxy-2-methyl-1-phenyl-propanone (Darocur0 1173, provided by BASF SE) as additional photoinitiator (C)

Formulation 9c: 1.0% by wt of the photoinitiator according to example 6 and 3.0% by wt of phenyl-1-hydroxycyclohexyl ketone (Irgacure® 184, provided by BASF SE) as additional photoinitiator (C)

Formulation 9d: 1.0% by wt of the photoinitiator according to example 6 and 3.0% by wt of methyl α-oxo benzeneacetate (Darocur® MBF, provided by BASF SE) as additional photoinitiator (C)

Formulation 9e: 1.0% by wt of the photoinitiator according to example 6 and 3.0% by wt of 2-hydroxy-1-{4-[4-(2-hydroxy-2-methyl-propionyl)-benzyl]-phenyl}-2-methyl-propan-1-one (Irgacure® 127, provided by BASF SE) as additional photoinitiator (C)

A9.1: Reactivity

The formulation to be tested is applied on white coil with a wet thickness of 100 µm. Curing of the formulation is achieved by moving the sample on a belt under a Hg lamp (200 W/cm) with a defined speed. The highest speed which can be used to fully cure the formulation is determined by finger nail scratch. The results are collected in the following table 6.

A9.2: Pendulum Hardness

The formulation to be tested is applied on white coil with a thickness of 100 µm. Curing of the formulation is achieved by moving the sample on a belt under a Hg lamp (120 W/cm) at a belt speed of 5 m/min. The pendulum hardness (PH) in seconds according to Konig DIN 53157 is determined after >24h storing in a temperature-controlled room at 22° C. The higher the PH value, the more reactive is the tested photoinitiator compound. The results are collected in the following table 6.

TABLE 6

| Example | Formulation 9a | Formulation 9b | Formulation 9c | Formulation 9d | Formulation 9e |
|---|---|---|---|---|---|
| A9.1; reactivity by belt speed [m/min] | 35 | 42.5 | 30 | 60 | 40 |
| A9.2: pendulum hardness [s] | 86 | 73 | 76 | 59 | 76 |

Example A10

Curing Performance of the of the Photoinitiator According to Example 6 in a Photocurable Water-Borne Clear and White Formulations Water-borne clear Formulations 10a-10b are prepared by mixing:

Formulation 10a:

| | |
|---|---|
| 100.0 g | of a water-based urethane acrylate dispersion (Laromer® WA 9057, provided by BASF SE) |
| 0.5 g | of a rheology modifier (DSX 1550 5% in water, provided by BASF SE) |
| 1.0 g | of the photoinitiator according to example 6 |

Formulation 10b:

| | |
|---|---|
| 100.0 g | of a water-emulsifiable polyester acrylate (Laromer® PE 22 WN, provided by BASF SE) |
| 0.5 g | of a rheology modifier (DSX 1550 5% in water, provided by BASF SE) |
| 1.0 g | of the photoinitiator according to example 6 |

Water-Borne White Formulations 10c-10d are Prepared by Mixing:

Formulation 10c:

| | |
|---|---|
| 100.0 g | of a water-based urethane acrylate dispersion (Laromer® WA 9057, provided by BASF SE) |
| 0.5 g | of a rheology modifier (DSX 1550 5% in water, provided by BASF SE) |
| 12.7 g | of an aqueous titanium dioxide pigment dispersion (Luconyl® NG white 0022, provided by BASF SE) |
| 1.0 g | of the photoinitiator according to example 6 |
| 1.2 g | of a photoinitiator blend of phenyl-1-hydroxycyclohexyl ketone and benzophenone in the ratio 1:1 (Irgacure® 500, provided by BASF SE) |

Formulation 10d:

| | |
|---|---|
| 100.0 g | of a water-emulsifiable polyester acrylate (Laromer® PE 22 WN, provided by BASF SE) |
| 0.5 g | of a rheology modifier (DSX 1550 5% in water, provided by BASF SE) |
| 12.7 g | of an aqueous titanium dioxide pigment dispersion (Luconyl® NG white 0022, provided by BASF SE) |
| 1.0 g | of the photoinitiator according to example 6 |
| 1.2 g | of a photoinitiator blend of phenyl-1-hydroxycyclohexyl ketone and benzophenone in the ratio 1:1 (Irgacure® 500, provided by BASF SE) |

A10.1: Reactivity

The formulation to be tested is applied on white aluminium coil panels with a wet thickness of 100 μm. The panels are then dried at 50° C. for 10 min. Curing of the formulation is achieved by moving the sample on a belt under two Hg lamp (120 W/cm) with at a belt speed of 5 m/min. Reactivity (through cure) is measured by the pendulum hardness (PH) in seconds according to König DIN 53157, determined after storing over night at room temperature. The higher the PH value, the more reactive is the tested photoinitiator compound.

Alternatively cure is also measured using the acetone double rub test, where an acetone soaked cotton ball is rubbed until the coating is removed. The higher the number of double rubs before the coating is removed, the better the curing efficiency of the photoinitiator.

The results are collected in the following table 7.

TABLE 7

| Example | Formulation 11a clear | Formulation 11b clear | Formulation 11c white | Formulation 11d white |
|---|---|---|---|---|
| A10.1: reactivity; pendulum hardness [s] | — | — | 71 | 84 |
| A10.2: reactivity; acetone double rubs | | | | |
| after curing | >200 | >200 | 99 | >200 |
| after 3 days | >200 | >200 | >200 | >200 |

Example A11

Curing Performance of the of the Photoinitiator According to Example 3 in a Photocurable Water-Borne White Pigmented Formulation A Water-Borne White Pigment Paste is Prepared by Mixing of the Following Ingredients:

| | |
|---|---|
| 48.2% | by wt of water |
| 6.0% | by wt of a wetting and dispersing additive (Disperbyk® 190, provided by BYK) |
| 1.0% | by wt of a defoamer (Dehydran® 1620, provided by BYK) |
| 0.8% | by wt of a hydrophilic fumed silica (Aerosil® 200, provided by Evonik), |
| 150.0% | by wt of a titanium dioxide white pigment for waterborne systems (Kronos® 2310, provided by Kronos) |

This Pigment Paste is Used for the Preparation of the Following Water-Borne White Lacquer:

| | |
|---|---|
| 256.0% | by wt of a water-borne UV curable polyurethane dispersion (Bayhydrol® UV XP 2629, provided by Bayer) |
| 40.0% | by wt of butylglycol/water 1:1 |
| 2.4% | by wt of a defoamer (BYK® 024, provided by BYK) |
| 4.0% | by wt a surfactant (BYK® 346, provided by BYK) |
| 0.8% | by wt a surface additive (BYK® 332, provided by BYK) |
| 176.0% | by wt of the white pigment paste as described above |
| 52.8% | by wt of water |
| 1.0% | by wt of the photoinitiator according to example 3 |

The following tests are undergone with samples of the formulation (a) directly after the preparation of the formulation (b) after 4 weeks of storing the formulation and (c) after 12 weeks of storing the formulation.

A11.1: Reactivity

The formulation to be tested is applied on white pre-coated aluminum panels coil with a wet thickness of 100 μm. The panels are then dried at 50° C. for 10 min. Curing of the formulation is achieved by moving the sample on a belt under two Hg lamp (100 W/cm) with at a belt speed of 10 m/min. The pendulum hardness (PH) in seconds according to Konig DIN 53157 is determined The higher the PH value, the more reactive is the tested photoinitiator compound. The results are collected in table 8.

A11.2: Gloss

The samples are prepared and cured as described in A10.1

Gloss is measured at 20°. The results are collected in the following table 8.

TABLE 8

| Example A10.1: pendulum hardness [s] | |
| --- | --- |
| immediately after preparation | 165 |
| after 4 weeks storage | 185 |
| after 12 weeks storage | 170 |
| Example A11.2: Gloss (GLU) | |
| immediately after preparation | 52 |
| after 4 weeks storage | 78 |
| after 12 weeks storage | 81 |

The invention claimed is:

1. A liquid photoinitiator mixture comprising the components (a) a compound of the formula (I)

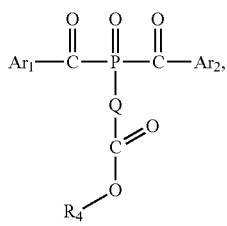

wherein $Ar_1$ and $Ar_2$ independently of each other are

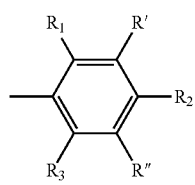

or naphthyl which is unsubstituted or substituted one or more times by $R_1$, $R_2$, $R_3$ or R';

$R_1$ and $R_3$ independently of each other are $C_1$-$C_4$alkyl, $C_1$-$C_4$alkoxy or halogen;

$R_2$ is hydrogen, $C_1$-$C_4$alkyl, halogen, $C_1$-$C_4$alkoxy or $C_2$-$C_{20}$alkoxy which is interrupted by one or more O;

Q is $C_1$-$C_4$alkylene;

$R_4$ is methyl or ethyl;

R' and R" independently of each other are hydrogen or PG-Y-R'''-X-;

PG is a polymerizable group or methyl or ethyl;

Y is a direct bond, O or S;

X is a direct bond, O or S;

R''' is a direct bond, $C_1$-$C_{20}$alkylene or $C_2$-$C_{20}$alkylene which is interrupted by one or more O;

(b) one or more compounds of the formula (II)

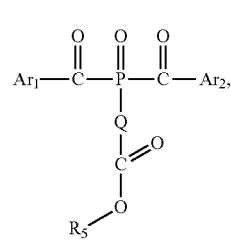

wherein $Ar_1$, $Ar_2$ and Q are as defined above, and $R_5$ is $C_3$-$C_{30}$alkyl which is unsubstituted or substituted by one or more of the groups selected from OH and

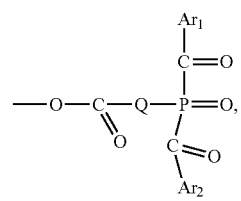

or $R_5$ is $C_2$-$C_{28}$alkyl which is interrupted by one or more O or $C_3$-$C_8$cycloalkylene and which interrupted $C_2$-$C_{28}$alkyl is unsubstituted or substituted by one or more of the groups selected from OH and

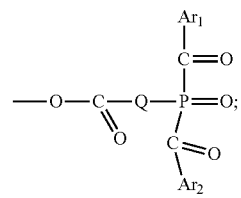

and (c) optionally a compound of the formula (III)

$R_5$—OH (III), wherein $R_5$ is as defined above.

2. The liquid photoinitiator mixture according to claim 1, wherein the mixture comprises 0.1-25% of component (a), 75-99.9% of component (b) and 0-25% of component (c).

3. The liquid photoinitiator mixture according to claim 1, wherein the compounds of the formula (I), (II) and (III)

$R_1$, $R_2$ and $R_3$ are $C_1$-$C_4$alkyl;

R' and R" are hydrogen;

Q is methylene, and $R_5$ is $C_3$-$C_{30}$alkyl which is unsubstituted or substituted by

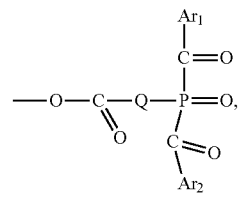

or $R_5$ is $C_2$-$C_{28}$alkyl which is interrupted by $C_3$-$C_8$cycloalkylene and which interrupted $C_3$-$C_{28}$alkyl is substituted by

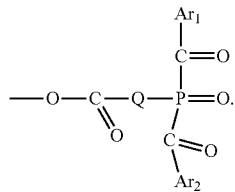

4. The liquid photoinitiator mixture according to claim 1, further comprising a further photoinitiator (C).

5. A photopolymerizable composition comprising
   (A) at least one monomeric or oligomeric ethylenically unsaturated photopolymerizable compound and
   (B) at least one liquid photoinitiator mixture according to claim 1.

6. The photopolymerizable composition according to claim 5, which further comprises at least one component selected from the group consisting of a photoinitiator (C) and other customary additives (D).

7. The photopolymerizable composition according to claim 6, wherein the additional photoinitiator (C) is selected from the group consisting of alpha-hydroxy ketones, benzophenone, substituted benzophenone compounds, benzildimethylketal, phenylglyoxylate compounds and alpha-amino ketone compounds.

8. The photopolymerizable composition according to claim 5, comprising 0.05 to 15% by weight of the liquid photoinitiator mixture (B) or the photoinitiators (B)+(C), based on the composition.

9. A process for the photopolymerization of monomeric, oligomeric or polymeric compounds containing at least one ethylenically unsaturated double bond, which comprises adding to the above mentioned compounds a liquid photoinitiator mixture according to claim 1 and irradiating the resulting composition with electromagnetic radiation.

10. A process according to claim 9 for producing coatings, printing inks, printing plates, adhesives, dental compositions, gel coats, photoresists for electronics, for encapsulating electrical and electronic components, for producing magnetic recording materials, for producing micromechanical parts, waveguides, optical switches, plating masks, etch masks, colour proofing systems, glass fibre cable coatings, screen printing stencils, for producing three-dimensional objects by a rapid prototyping or additive manufacturing technology based on a photolithographic or polymer jetting process using light curable materials, for producing image recording material, for holographic recording, for producing microelectronic circuits or for producing decolorizing materials.

11. A coated substrate which is coated on at least one surface with the composition according to claim 5 and irradiated with electromagnetic radiation.

12. A polymerized or crosslinked composition obtained by curing the polymerizable composition according to claim 5.

13. A process for the preparation of the liquid photoinitiator mixture as defined in claim 1, comprising reacting the compound of the formula (I),
with an alcohol of the formula (III)

$$R_5\text{—OH} \qquad (III),$$

wherein
   $R_5$ is as defined in claim 1,
   in the presence of a catalyst and taking means to remove the alcohol of the formula (IV) which is formed during the reaction $$R_4\text{—OH} \qquad (IV),$$

wherein
   $R_4$ is methyl or ethyl.

14. The photopolymerizable composition according to claim 5, comprising 0.1 to 5% by weight of the liquid photoinitiator mixture (B) or the photoinitiators (B)+(C), based on the composition.

* * * * *